US012311000B2

(12) United States Patent
Borad et al.

(10) Patent No.: US 12,311,000 B2
(45) Date of Patent: May 27, 2025

(54) CHIMERIC VESICULOVIRUSES AND METHODS OF USE

(71) Applicant: Mayo Foundation for Medical Education and Research, Rochester, MN (US)

(72) Inventors: Mitesh J. Borad, Tempe, AZ (US); Bolni M. Nagalo, Tempe, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 637 days.

(21) Appl. No.: 17/635,161

(22) PCT Filed: Aug. 14, 2020

(86) PCT No.: PCT/US2020/046503
§ 371 (c)(1),
(2) Date: Feb. 14, 2022

(87) PCT Pub. No.: WO2021/034710
PCT Pub. Date: Feb. 25, 2021

(65) Prior Publication Data

US 2022/0273740 A1 Sep. 1, 2022

Related U.S. Application Data

(60) Provisional application No. 62/887,991, filed on Aug. 16, 2019.

(51) Int. Cl.
*A61K 35/766* (2015.01)
*A61P 35/00* (2006.01)
*C12N 7/00* (2006.01)

(52) U.S. Cl.
CPC ............ *A61K 35/766* (2013.01); *A61P 35/00* (2018.01); *C12N 7/00* (2013.01); *C12N 2760/20221* (2013.01); *C12N 2760/20232* (2013.01)

(58) Field of Classification Search
None
See application file for complete search history.

(56) References Cited

U.S. PATENT DOCUMENTS

| | | | | |
|---|---|---|---|---|
| 2005/0238656 | A1 | 10/2005 | Rose | |
| 2006/0127981 | A1 | 6/2006 | Bergman et al. | |
| 2007/0184069 | A1 | 8/2007 | Buchholz et al. | |
| 2009/0220539 | A1 | 9/2009 | Angela et al. | |
| 2011/0052539 | A1* | 3/2011 | Stojdl | A61P 35/00 435/235.1 |
| 2014/0142160 | A1 | 5/2014 | Lee et al. | |
| 2020/0216502 | A1 | 7/2020 | Albertini et al. | |
| 2020/0237838 | A1 | 7/2020 | Mueller et al. | |

FOREIGN PATENT DOCUMENTS

| | | |
|---|---|---|
| WO | WO 2019/057974 | 3/2019 |
| WO | WO 2021034710 | 2/2021 |

OTHER PUBLICATIONS

Walker et al., "Evolution of Genome Size and Complexity in the Rhabdoviridae", PLOS Pathogens, vol. 11, article e1004664; pp. 1-25 (Year: 2015).*
Ahmed et al., "Ability of the matrix protein of vesicular stomatitis virus to suppress beta interferon gene expression is genetically correlated with the inhibition of host RNA and protein synthesis," J. Virology, Apr. 15, 2003, 77(8):4646-4657.
Altschul et al., "Gapped BLAST and PSI-BLAST: a new generation of protein database search programs," Nucleic Acids Research, Sep. 1, 1997, 25(17):3389-3402.
Amarasinghe et al., "Taxonomy of the order Mononegavirales: update 2017," Arch. Virology, Aug. 2017, 162(8):2493-2504.
Betancourt et al., "Retargeting Oncolytic Vesicular Stomatitis Virus to Human T-Cell Lymphotropic Virus Type 1-Associated Adult T-Cell Leukemia," J. Virology, Sep. 16, 2015, 89(23):11786-11800.
Bishnoi et al., "Oncotargeting by Vesicular Stomatitis Virus (VSV): Advances in Cancer Therapy," Viruses, Feb. 23, 2018, 10(2):90, 20 pages.
Blasdell et al., "Ledantevirus: A Proposed New Genus in the *Rhabdoviridae* Has a Strong Ecological Association with Bats," Am. J. Trop. Med. Hygiene, Feb. 2015, 92(2):405-410.
Dietzgen et al., "The family Rhabdoviridae: mono- and bipartite negative-sense RNA viruses with diverse genome organization and common evolutionary origins," Virus Research, Jan. 2, 2017, 227:158-170.
Fuchs et al., "First-in-Human Evaluation of the Safety and Immunogenicity of a Recombinant Vesicular Stomatitis Virus Human Immunodeficiency Virus-1 gag Vaccine (HVTN 090)," Open Forum Infect. Diseases, Jun. 5, 2015, 2(3):ofv082, 9 pages.
GenBank Accession No. J02428.1, "Vesicular stomatitis Indiana virus, complete genome," dated Oct. 21, 2002, 7 pages.
GenBank Accession No. KM205007.1, "Morreton virus nucleoprotein, phosphoprotein, matrix, glycoprotein, and polymerase genes, complete cds," dated Mar. 10, 2015, 5 pages.
GenBank Accession No. KT429217.1, "Vesicular stomatitis virus strain Arizona/5481555/2015, complete genome," dated Feb. 2, 2016, 5 pages.
GenBank Accession No. NC_001560.1, "Vesicular stomatitis Indiana virus, complete genome," dated Aug. 13, 2018, 8 pages.
GenBank Accession No. NC_034508.1, "Morreton virus nucleoprotein, phosphoprotein, matrix, glycoprotein, and polymerase genes, complete cds," dated Aug. 13, 2018, 5 pages.

(Continued)

*Primary Examiner* — Michelle F. Paguio Frising
(74) *Attorney, Agent, or Firm* — Fish & Richardson P.C.

(57) ABSTRACT

The disclosure provides methods and materials for treating cancer. Specifically, the disclosure provides a chimeric vesiculovirus comprising: (a) a first genomic fragment of a first vesiculovirus species; and (b) a second genomic fragment of a second vesiculovirus species different from said first vesiculovirus species; wherein the vesiculovirus species comprising vesicular stomatitis viruses (VSVs) and morreton Virus (MorV). Further disclosed are methods of using chimeric vesiculoviruses as oncolytic agents for treating cancer.

18 Claims, 15 Drawing Sheets

Specification includes a Sequence Listing.

(56) References Cited

OTHER PUBLICATIONS

Johnson et al., "Neurovirulence properties of recombinant vesicular stomatitis virus vectors in non-human primates," Virology, Mar. 30, 2007, 360(1):36-49.
Lawson et al., "Recombinant vesicular stomatitis viruses from DNA," Proc. Natl. Acad. Sci. USA, May 9, 1995, 92(10):4477-4481.
Muik et al., "Re-engineering vesicular stomatitis virus to abrogate neurotoxicity, circumvent humoral immunity, and enhance oncolytic potency," Cancer Research, Jul. 1, 2014, 74(13):3567-3578.
Munis et al., "Characterization of Antibody Interactions with the G Protein of Vesicular Stomatitis Virus Indiana Strain and Other Vesiculovirus G Proteins," J. Virology, Nov. 12, 2018, 92(23):000900-18, 14 pages.
Murphy et al., "Vesicular stomatitis virus as an oncolytic agent against pancreatic ductal adenocarcinoma," J. Virology, Mar. 2012, 86(6):3073-3087.
Naik et al., "Potent systemic therapy of multiple myeloma utilizing oncolytic vesicular stomatitis virus coding for interferon-β," Cancer Gene Therapy, Jul. 2012, 19(7):443-450.
Patel et al., "Vesicular stomatitis virus expressing interferon-β is oncolytic and promotes antitumor immune responses in a syngeneic murine model of non-small cell lung cancer," Oncotarget, Oct. 20, 2015, 6(32):33165-33177.
PCT International Preliminary Report on Patentability in International Appln. No. PCT/US2020/046503, dated Feb. 17, 2022, 8 pages.
PCT International Search Report and Written Opinion in International Appln. No. PCT/US2020/046503, dated Feb. 9, 2021, 15 pages.
Quiroz et al., "A human case of encephalitis associated with vesicular stomatitis virus (Indiana serotype) infection," Am. J. Trop. Med. Hygiene, Sep. 1988, 39(3):312-314.
Russell et al., "Oncolytic Virotherapy: A Contest between Apples and Oranges," Mol. Therapy, May 3, 2017, 25(5):1107-1116.
Sharif-Askari et al., "Bax-dependent mitochondrial membrane permeabilization enhances IRF3-mediated innate immune response during VSV infection," Virology, Aug. 15, 2007, 365(1):20-33.
Shinozaki et al., "Eradication of advanced hepatocellular carcinoma in rats via repeated hepatic arterial infusions of recombinant VSV," Hepatology, Jan. 2005, 41(1):196-203.
Walker et al., "Evolution of genome size and complexity in the rhabdoviridae," PLoS Pathogens, Feb. 13, 2015, 11(2):e1004664, 26 pages.
Zhang et al., "Safety Studies in Tumor and Non-Tumor-Bearing Mice in Support of Clinical Trials Using Oncolytic VSV-IFNβ-NIS," Hum. Gene Ther. Clin. Development, Sep. 2016, 27(3):111-122.
Extended European Search Report in European AppIn No. 20855782.7, dated Aug. 7, 2023, 11 pages.
Koske et al., "Oncolytic virotherapy enhances the efficacy of a cancer vaccine by modulating the tumor microenvironment," Int. J. Cancer, Apr. 2019, 145(7):1958-1969.
Watters et al., "Multi-modal efficacy of a chimeric vesiculovirus expressing the Morreton glycoprotein in sarcoma," Mol. Ther. Oncolytics, Jun. 2023, 29:4-14.
ICTV.global [online], "Family: Rhabdoviridae," 2022, retrieved on Jan. 7, 2025, retrieved from URL<https://ictv.global/report/chapter/rhabdoviridae/rhabdoviridae>, 60 pages.
Walker et al., "ICTV Virus Taxonomy Profile: Rhabdoviridae 2022," J. Gen. Virol., Jun. 2022, 103(6):001689.
Alain et al., "Vesicular stomatitis virus oncolysis is potentiated by impairing mTORC1-dependent type I IFN production," PNAS, Jan. 26, 2010, 107(4):1576-1581.
Altomonte et al., "Antifibrotic Properties of Transarterial Oncolytic VSV Therapy for Hepatocellular Carcinoma in Rats With Thioacetamide-Induced Liver Fibrosis," Molecular Therapy, Nov. 2013, 21(11):2032-2042.
Beebe et al., "Neutralization of vesicular stomatitis virus (VSV) by human complement requires a natural IgM antibody present in human serum," The Journal of Immunology, Apr. 1981, 126(4):1562-1568.
Chiocca et al., "Oncolytic Viruses and Their Application to Cancer Immunotherapy," Cancer Immunology at the Crossroads: Experimental Immunotherapies, Apr. 3, 2014, 2(4):295-300.
clinicaltrials.gov [online], "Viral Therapy in Treating Patient With Refractory Liver Cancer or Advanced Solid Tumors," Available on or before Dec. 2, 2023, via Internet Archive: Wayback Machine URL <https://web.archive.org/web/20231202120122/http://clinicaltrials.gov/study/NCT01628640>, retrieved on Oct. 9, 2024, URL <http://clinicaltrials.gov/study/NCT01628640>, 11 pages.
Essletzbichler et al., "Megabase-scale deletion using CRISPR/Cas9 to generate a fully haploid human cell line," Genome Research, 2014, pp. 2059-2065.
Faul et al., "Interferon Response and Viral Evasion by Members of the Family Rhabdoviridae," Viruses, Nov. 9, 2009, 1:832-851.
Felsenstein, "Confidence Limits on Phylogenies: An Approach Using the Bootstrap," Evolution, 1985, 39(4):783-791.
Felt et al., "Recent advances in vesicular stomatitis virus-based oncolytic virotherapy: a 5-year update," Journal of General Virology, Dec. 2017, 98(12):2895-2911.
Finkelshtein et al., "LDL receptor and its family members serve as the cellular receptors for vesicular stomatitis virus," PNAS, Apr. 30, 2013, 110(18):7306-7311.
Garijo et al., "Constrained evolvability of interferon suppression in an RNA virus," Scientific Reports, Apr. 21, 2016, 6(24722):1-10.
Gong et al., "Immunoglobulin M: An Ancient Antiviral Weapon—Rediscovered," Front. Immunol., Aug. 10, 2020, 11(1943):1-9, 9 pages.
Harrington et al., "Clinical development of talimogene laherparepvec (T-VEC): a modified herpes simplex virus type-1-derived oncolytic immunotherapy," Expert Review of Anticancer Therapy, Dec. 3, 2015, 15(12):1389-1403.
International Preliminary Report on Patentability in International Appln. No. PCT/US2023/63569, mailed Sep. 24, 2024, 10 pages.
International Search Report and Written Opinion in International Appln. No. PCT/US2023/63569, mailed Aug. 23, 2023, 14 pages.
Jones et al., "The rapid generation of mutation data matrices from protein sequences," Comput. Appl. Biosci., Jun. 1992, 8(3):275-282.
Kamphuis et al., "Type I interferons directly regulate lymphocyte recirculation and cause transient blood lymphopenia," Blood, Nov. 15, 2006, 108(10):3253-3261.
Kane et al., "Sui generis: gene therapy and delivery systems for the treatment of glioblastoma," Neuro-Oncology, Mar. 2015, 17(S2):ii24-ii36.
Kaufman et al., "Oncolytic viruses: a new class of immunotherapy drugs," Nature Reviews Drug Discovery, Sep. 2015, 14:642-662.
Kravtsova-Ivantsiv et al., "KPC1-mediated ubiquitination and proteasomal processing of NF-kappaB1 p105 to p50 restricts tumor growth," Cell, Apr. 9, 2015, 161(2):333-347.
Kumar et al., "MEGA X: Molecular Evolutionary Genetics Analysis across Computing Platforms," Molecular Biology and Evolution, Jun. 2018, 35(6):1547-1549.
Kunze et al., "Localization of the active type I DNA topoisomerase gene on human chromosome 20q11.2-13.1, and two pseudogenes on chromosomes 1q23-24 and 22q11.2- 13.1," Human Genetics, Dec. 1989, 84:6-10.
Lawler et al., "Oncolytic Viruses in Cancer Treatment: A Review," JAMA Oncology, Published online Jul. 21, 2016, pp. E1-E9.
Liu et al., "Vesicular Stomatitis Virus: From Agricultural Pathogen to Vaccine Vector," Pathogens, Aug. 27, 2021, 10(1092):1-20.
Loeuillard et al., "Targeting tumor-associated macrophages and granulocytic myeloid-derived suppressor cells augments PD-1 blockade in cholangiocarcinoma," The Journal of Clinical Investigation, Oct. 2020, 130(10):5380-5396.
Machiels et al., "A phase 1 dose escalation study of the oncolytic adenovirus enadenotucirev, administered intravenously to patients with epithelial solid tumors (EVOLVE)," Journal for Immuno Therapy of Cancer, 2019, 7(20):1-15.

(56) References Cited

OTHER PUBLICATIONS

Martuza et al., "Experimental Therapy of Human Glioma by Means of a Genetically Engineered Virus Mutant," Science, May 10, 1991, 252(5007):854-856.

Nagalo et al., "Characterization of Morreton Virus (MORV) as a Novel Oncolytic Virotherapy Platform for Liver Cancers," bioRxiv, Mar. 11, 2022, 51 pages.

ncbi.nlm.nih.gov [online], "Morreton virus nucleoprotein, phosphoprotein, matrix, glycoprotein, and polymerase genes, complete cds," Submitted Jul. 15, 2014, retrieved on Oct. 9, 2024, retrieved from URL <https://www.ncbi.nlm.nih.gov/nuccore/KM205007>, 5 pages.

Obuchi et al., "Development of Recombinant Vesicular Stomatitis Viruses That Exploit Defects in Host Defense to Augment Specific Oncolytic Activity," Journal of Virology, Aug. 2003, 77(16):8843-8856.

Rizvi et al., "YAP-associated chromosomal instability and cholangiocarcinoma in mice," Oncotarget, Dec. 22, 2017, 9(5):5892-5905.

Russell et al., "Oncolytic virotherapy," Nature Biotechnology, Jul. 10, 2012, 30(7):1-13.

Sanchez et al., "Perinatal Nutritional Reprogramming of the Epigenome Promotes Subsequent Development of Nonalcoholic Steatohepatitis," Hepatology Communications, Dec. 2018, 2(12):1493-1512.

Schattner et al., "Involvement of interferon in virus-induced lymphopenia," Cellular Immunology, Jul. 1, 1983, 79(1):11-25.

Snell et al., "Type I Interferon in Chronic Virus Infection and Cancer," Trends in Immunology, Aug. 2017, 38(8):542-557.

Stojdl et al., "Exploiting tumor-specific defects in the interferon pathway with a previously unknown oncolytic virus," Nature Medicine, Jul. 2000, 6(7):821-825.

Tang et al., "PD-L1 on host cells is essential for PD-L1 blockade-mediated tumor regression," The Journal of Clinical Investigation, 2018, 128(2):580-588.

Teicher, "Tumor models for efficacy determination," Molecular Cancer Therapeutics, Oct. 13, 2006, 5(10):2435-2443.

Tesfay et al., "Vesiculovirus Neutralization by Natural IgM and Complement," Journal of Virology, Jun. 2014, 88(11):6148-6157.

Tesh et al., "Natural Infection of Humans, Animals, and Phlebotomine Sand Flies with the Alagoas Serotype of Vesicular Stomatitis Virus in Colombia," The American Journal of Tropical Medicine and Hygiene, May 1987, 36(3):653-661, Abstract Only.

Whelan et al., "Efficient recovery of infectious vesicular stomatitis virus entirely from cDNA clones," Proc. Natl. Acad. Sci. USA, Aug. 29, 1995, 92(18):8388-8392.

Yamada et al., "IL-33 facilitates oncogene-induced cholangiocarcinoma in mice by an interleukin-6-sensitive mechanism," Hepatology, May 2015, 61(5):1627-1642.

Yuan et al., "NUAK2 is a critical YAP target in liver cancer," Nature Communications, Nov. 16, 2018, 9(4834):1-12.

Zemp et al., "Rhabdoviruses as vaccine platforms for infectious disease and cancer," Biotechnology and Genetic Engineering Reviews, May 21, 2018, 34(1):122-138.

Zeyaullah et al., "Oncolytic Viruses in the Treatment of Cancer: A Review of Current Strategies," Pathology & Oncology Research, Jun. 20, 2012, 18(4):771-781.

U.S. Appl. No. 18/849,044, filed Sep. 20, 2024, Mitesh J. Borad, Pending.

* cited by examiner

> VSV-MorV-G complet e sequence

VSV-N

ATCATTAAAAGGCTCAGGAGAAACTTTAACAGTAATCAAAATGTCTGTTACAGTCAAGAGAATCATTGACAACAC
AGTCGTAGTTCCAAAACTTCCTGCAAATGAGGATCCAGTGGAATACCCGGCAGATTACTTCAGAAAATCAAAGGA
GATTCCTCTTTACATCAATACTACAAAAAGTTTGTCAGATCTAAGAGGATATGTCTACCAAGGCCTCAAATCCGGAA
ATGTATCAATCATACATGTCAACAGCTACTTGTATGGAGCATTAAAGGACATCCGGGGTAAGTTGGATAAAGATTG
GTCAAGTTTCGGAATAAACATCGGGAAAGCAGGGGATACAATCGGAATATTTGACCTTGTATCCTTGAAAGCCCT
GGACGGCGTACTTCCAGATGGAGTATCGGATGCTTCCAGAACCAGCGCAGATGACAAATGGTTGCCTTTGTATCT
ACTTGGCTTATACAGAGTGGGCAGAACACAAATGCCTGAATACAGAAAAAAGCTCATGGATGGGCTGACAAATCA
ATGCAAAATGATCAATGAACAGTTTGAACCTCTTGTGCCAGAAGGTCGTGACATTTTTGATGTGTGGGGAAATGAC
AGTAATTACACAAAAATTGTCGCTGCAGTGGACATGTTCTTCCACATGTTCAAAAAACATGAATGTGCCTCGTTCA
GATACGGAACTATTGTTTCCAGATTCAAAGATTGTGCTGCATTGGCAACATTTGGACACCTCTGCAAAATAACCGG
AATGTCTACAGAAGATGTAACGACCTGGATCTTGAACCGAGAAGTTGCAGATGAAATGGTCCAAATGATGCTTCC
AGGCCAAGAAATTGACAAGGCCGATTCATACATGCCTTATTTGATCGACTTTGGATTGTCTTCTAAGTCTCCATATT
CTTCCGTCAAAAACCCTGCCTTCCACTTCTGGGGGCAATTGACAGCTCTTCTGCTCAGATCCACCAGAGCAAGGAA
TGCCCGACAGCCTGATGACATTGAGTATACATCTCTTACTACAGCAGGTTTGTTGTACGCTTATGCAGTAGGATCCT
CTGCCGACTTGGCACAACAGTTTTGTGTTGGAGATAACAAATACACTCCAGATGATAGTACCGGAGGATTGACGA
CTAATGCACCGCCACAAGGCAGAGATGTGGTCGAATGGCTCGGATGGTTTGAAGATCAAAACAGAAAACCGACTC
CTGATATGATGCAGTATGCGAAAAGAGCAGTCATGTCACTGCAAGGCCTAAGAGAGAAGACAATTGGCAAGTAT
GCTAAGTCAGAATTTGACAAATGACCCTATAATTCTCAGATCACCTATTATATATTATGCTACATATGAAAAAAAC
TAACAGATATCATGGATAATCTCACAAAAGTTCGTGAGTATCTCAAGTCCTATTCTCGTCTGGATCAGGCGGTAGG

VSV-P

AGAGATAGATGAGATCGAAGCACAACGAGCTGAAAAGTCCAATTATGAGTTGTTCCAAGAGGATGGAGTGGAAG
AGCATACTAAGCCCTCTTATTTTCAGGCAGCAGATGATTCTGACACAGAATCTGAACCAGAAATTGAAGACAATCA
AGGCTTGTATGCACCAGATCCAGAAGCTGAGCAAGTTGAAGGCTTTATACAGGGGCCTTTAGATGACTATGCAGA
TGAGGAAGTGGATGTTGTATTTACTTCGGACTGGAAACAGCCTGAGCTTGAATCTGACGAGCATGGAAAGACCTT
ACGGTTGACATCGCCAGAGGGTTTAAGTGGAGAGCAGAAATCCCAGTGGCTTTCGACGATTAAAGCAGTCGTGCA
AAGTGCCAAATACTGGAATCTGGCAGAGTGCACATTTGAAGCATCGGGAGAAGGGGTCATTATGAAGGAGCGCC
AGATAACTCCGGATGTATATAAGGTCACTCCAGTGATGAACACACATCCGTCCCAATCAGAAGCAGTATCAGATGT

TTGGTCTCTCTCAAAGACATCCATGACTTTCCAACCCAAGAAAGCAAGTCTTCAGCCTCTCACCATATCCTTGGATG
AATTGTTCTCATCTAGAGGAGAGTTCATCTCTGTCGGAGGTGACGGACGAATGTCTCATAAAGAGGCCATCCTGCT
CGGCCTGAGATACAAAAAGTTGTACAATCAGGCGAGAGTCAAATATTCTCTGTAGACTATGAAAAAAAGTAACA
GATATCACGATCTAAGTGTTATCCCAATCCATTCATCATGAGTTCCTTAAAGAAGATTCTCGGTCTGAAGGGGAAA VSV-M
GGTAAGAAATCTAAGAAATTAGGGATCGCACCACCCCTTATGAAGAGGACACTAGCATGGAGTATGCTCCGAGC
GCTCCAATTGACAAATCCTATTTTGGAGTTGACGAGATGGACACCTATGATCCGAATCAATTAAGATATGAGAAAT
TCTTCTTTACAGTGAAAATGACGGTTAGATCTAATCGTCCGTTCAGAACATACTCAGATGTGGCAGCCGCTGTATCC
CATTGGGATCACATGTACATCGGAATGGCAGGGAAACGTCCCTTCTACAAAATCTTGGCTIT11TGGGTTCTTCTAA
TCTAAAGGCCACTCCAGCGGTATTGGCAGATCAAGGTCAACCAGAGTATCACGCTCACTGCGAAGGCAGGGCTTA
TTTGCCACATAGGATGGGGAAGACCCCTCCCATGCTCAATGTACCAGAGCACTTCAGAAGACCATTCAATATAGGT
CTTTACAAGGGAACGATTGAGCTCACAATGACCATCTACGATGATGAGTCACTGGAAGCAGCTCCTATGATCTGG
GATCATTTCAATTCTTCCAAAITTTCTGATTTCAGAGAGAAGGCCTTAATGTTTGGCCTGATTGTCGAGAAAAAGGC
ATCTGGAGCGTGGGTCCTGGACTCTATCGGCCACTTCAAATGAGCTAGTCTAACTTCTAGCTTCTGAACAATCCCC
GGTTTACTCAGTCTCCCCTAATTCCAGCCTCTCGAACAACTAATATCCTGTCTTTTCTATCCCTATGAAAAAAACTA
ACAGAGATCGATCTGTTTACGCGTATCATTCTGTTTCGTCACTATGCTGGTTTTATACCTGTTATTGAGCCTTTTGG MorV-G
CTCTGGGAGCTCAATGCAAGTTCACTATAGTATTTCCTCACAATCAAAAAGGGAATTGGAAAAATGTACCGGCAAA
TTATCAGTATTGTCCTTCTAGTTCTGACTTGAATTGGCACAATGGGCTGATTGGCACTTCTCTCCAAGTCAAAATGC
CCAAAAGCCATAAGGCCATCCAAGCGGATGGTTGGATGTGTCATGCTGCCAAGTGGGTGACTACTTGTGACTTCA
GATGGTACGGACCTAAATATGTGACACATTCTATAAAGTCCATGATACCTACAGTCGACCAGTGTAAAGAAAGTAT
AGCCCAGACTAAACAAGGAACGTGGTTAAATCCGGGTTTCCCTCCCCAAAGTTGTGGATATGCTTCCGTTACAGAT
GCAGAGGCTGTGATAGTCAAAGCAACCCCCCACCAGGTTTTGGTTGACGAATATACAGGAGAATGGGTTGACTCC
CAATTTCCGACTGGAAAATGCAATAAAGACATTTGCCCAACAGTTCACAACTCAACTACCTGGCACTCAGATTATAA
GGTCACTGGCCTTTGCGATGCAAATTTGATCTCAATGGACATCACTTTCTTCTCCGAAGATGGAAAATTAACATCCC
TCGGGAAAGAAGGAACAGGGTTCAGAAGCAATTACTTTGCATACGAAAATGGTGACAAAGCATGCCGCATGCAG
TACTGTAAACACTGGGGAGTTCGACTTCCATCCGGAGTGTGGTTCGAAATGGCAGATAAAGACATCTATAATGAT
GCGAAATTCCCGGATTGCCCTGAAGGATCATCCATTGCGGCTCCCTCTCAGAITTCAGTCGATGTTAGTCTCATTCA
GGATGTAGAGAGAATCTTGGACTACTCTTTGTGTCAGGAAACCTGGAGCAAAATTCGTGCTCATTTGCCCATTTCA
CCAGTTGACCTCAGCTATTTATCCCCAAAAAATCCTGGAACTGGTCCTGCATTCACTATCATCAATGGGACATTAAA

*ATACTTTGAGACTCGATACATAAGAGTCGATATCGCAGGACCCATCATTCCTCAAATGAGAGGAGTAATCAGcGGA*
*ACCACGACCGAGAGAGAgCTGTGGACGGACTGGTaCCCCTACGAAGATGTTGAAATCGGACCAAATGGGGITITG*
*AAAACTGCTACAGGGTATAAGTTCCCTTTATACATGATTGGCCACGGCATGCTCGACTCAGATCTCCACATCTCATC*
*AAAGGCTCAGGTTTTTGAACATCCCCATATTCAGGATGCTGCTTCTCAGCTTCCTGATGATGAGACTTTATTTTTTG*
*GTGATACTGGACTCTCGAAAAACCCCATAGAGCTTGTAGAAGGTTGGTTCAGCGGATGGAAAAGCACTATTGCttT*
*CTTTTTTCTTCATAATAGGGCTTGTGATCGGATTATAttTTGGTTCTTAGGATTGGAATCGCTTTATGCATCAAATGC*
*CGAGTGCAGGAGAAAAGGCCCAAAATTTACACTGATGTGGAAATGA*ACAGATTGGATCGAT*GAAAGCTTCATTG*
*CTGCAGATGACAACCACACTCACCAAAG*GCTAGCCAGATTCTTCATGTTTGGACCAAATCAACTTGTGATACCAT
GCTCAAAGAGGCCTCAATTATATTTGAGTTTTTAATTTTTATGAAAAAAACTAACAGCAATC*ATGGAAGTCCACG* VSV-L
*ATTTTGAGACCGACGAGTTCAATGATTTCAATGAAGATGACTATGCCACAAGAGAATTCCTGAATCCCGATGAGCG*
*CATGACGTACTTGAATCATGCTGATTACAACCTGAATTCTCCTCTAATTAGTGATGATATTGACAATTTAATCAGGA*
*AATTCAATTCTCTTCCAATTCCCTCGATGTGGGATAGTAAGAACTGGGATGGAGTTCTTGAGATGTTAACGTCATGT*
*CAAGCCAATCCCATCCCAACATCTCAGATGCATAAATGGATGGGAAGTTGGTTAATGTCTGATAATCATGATGCCA*
*GTCAAGGGTATAGTTTTTACATGAAGTGGACAAAGAGGCAGAAATAACATTTGACGTGGTGGAGACCTTCATCC*
*GCGGCTGGGGCAACAAACCAATTGAATACATCAAAAAGGAAAGATGGACTGACTCATTCAAAATTCTCGCTTATTT*
*GTGTCAAAAGTTTTTGGACTTACACAAGTTGACATTAATCTTAAATGCTGTCTCTGAGGTGGAATTGCTCAACTTGG*
*CGAGGACTTTCAAAGGCAAAGTCAGAAGAAGTTCTCATGGAACGAACATATGCAGGATTAGGGTTCCCAGCTTGG*
*GTCCTACTTTTATTTCAGAAGGATGGGCTTACTTCAAGAAACTTGATATTCTAATGGACCGAAACTTTCTGTTAATG*
*GTCAAAGATGTGATTATAGGGAGGATGCAAACGGTGCTATCCATGGTATGTAGAATAGACAACCTGTTCTCAGAG*
*CAAGACATCTTCTCCCTTCTAAATATCTACAGAATTGGAGATAAAATTGTGGAGAGGCAGGGAAATTTTTCTTATG*
*ACTTGATTAAAATGGTGGAACCGATATGCAACTTGAAGCTGATGAAATTAGCAAGAGAATCAAGGCCTTTAGTCCC*
*ACAATTCCCTCATTTTGAAAATCATATCAAGACTTCTGTTGATGAAGGGGCAAAAATTGACCGAGGTATAAGATTC*
*CTCCATGATCAGATAATGAGTGTGAAAACAGTGGATCTCACACTGGTGATTTATGGATCGTTCAGACATTGGGGTC*
*ATCCTTTTATAGATTATTACACTGGACTAGAAAAATTACATTCCCAAGTAACCATGAAGAAAGATATTGATGTGTCA*
*TATGCAAAAGCACTTGCAAGTGATTTAGCTCGGATTGTTCTATTTCAACAGTTCAATGATCATAAAAAGTGGTTCGT*
*GAATGGAGACTTGCTCCCTCATGATCATCCCTTTAAAAGTCATGTTAAAGAAAATACATGGCCCACAGCTGCTCAA*
*GTTCAAGATTTTGGAGATAAATGGCATGAACTTCCGCTGATTAAATGTTTTGAAATACCCGACTTACTAGACCCATC*
*GATAATATACTCTGACAAAAGTCATTCAATGAATAGGTCAGAGGTGTTGAAACATGTCCGAATGAATCCGAACACT*

CCTATCCCTAGTAAAAAGGTGTTGCAGACTATGTTGGACACAAAGGCTACCAATTGGAAAGAATTTCTTAAAGAGA
TTGATGAGAAGGGCTTAGATGATGATGATCTAATTATTGGTCTTAAAGGAAAGGAGAGGGAACTGAAGTTGGCA
GGTAGATITTTCTCCCTAATGTCTTGGAAATTGCGAGAATACTTTGTAATTACCGAATATTTGATAAAGACTCATTTC
GTCCCTATGTTTAAAGGCCTGACAATGGCGGACGATCTAACTGCAGTCATTAAAAAGATGTTAGATTCCTCATCCG
GCCAAGGATTGAAGTCATATGAGGCAATTTGCATAGCCAATCACATTGATTACGAAAAATGGAATAACCACCAAA
GGAAGTTATCAAACGGCCCAGTGTTCCGAGTTATGGGCCAGTTCTTAGGTTATCCATCCTTAATCGAGAGAACTCA
TGAATTTTTTGAGAAAAGTCTTATATACTACAATGGAAGACCAGACTTGATGCGTGTTCACAACAACACACTGATC
AATTCAACCTCCCAACGAGTTTGTTGGCAAGGACAAGAGGGTGGACTGGAAGGTCTACGGCAAAAAGGATGGAG
TATCCTCAATCTACTGGTTATTCAAAGAGAGGCTAAAATCAGAAACACTGCTGTCAAAGTCTTGGCACAAGGTGAT
AATCAAGTTATTTGCACACAGTATAAAACGAAGAAATCGAGAAACGTTGTAGAATTACAGGGTGCTCTCAATCAAA
TGGTTTCTAATAATGAGAAAATTATGACTGCAATCAAAATAGGGACAGGGAAGTTAGGACTTTTGATAAATGACG
ATGAGACTATGCAATCTGCAGATTACTTGAATTATGGAAAAATACCGATTTTCCGTGGAGTGATTAGAGGGTTAGA
GACCAAGAGATGGTCACGAGTGACTTGTGTCACCAATGACCAAATACCCACITGTGCTAATATAATGAGCTCAGTT
TCCACAAATGCTCTCACCGTAGCTCATTTTGCTGAGAACCCAATCAATGCCATGATACAGTACAATTATTTTGGGAC
ATTTGCTAGACTCTTGTTGATGATGCATGATCCTGCTCTTCGTCAATCATTGTATGAAGTTCAAGATAAGATACCGG
GCTTGCACAGTTCTACTTTCAAATACGCCATGTTGTATTTGGACCCTTCCATTGGAGGAGTGTCGGGCATGTCTTTG
TCCAGGTTTTTGATTAGAGCCTTCCCAGATCCCGTAACAGAAAGTCTCTCATTCTGGAGATTCATCCATGTACATGC
TCGAAGTGAGCATCTGAAGGAGATGAGTGCAGTATTTGGAAACCCCGAGATAGCCAAGTTTCGAATAACTCACAT
AGACAAGCTAGTAGAAGATCCAACCTCTCTGAACATCGCTATGGGAATGAGTCCAGCGAACTTGTTAAAGACTGA
GGTTAAAAAATGCTTAATCGAATCAAGACAAACCATCAGGAACCAGGTGATTAAGGATGCAACCATATATTTGTAT
CATGAAGAGGATCGGCTCAGAAGTTTCTTATGGTCAATAAATCCTCTGTTCCCTAGATTTTTAAGTGAATTCAAATC
AGGCACTTTTTTGGGAGTCGCAGACGGGCTCATCAGTCTATTTCAAAATTCTCGTACTATTCGGAACTCCTTTAAGA
AAAAGTATCATAGGGAATTGGATGATTTGATTGTGAGGAGTGAGGTATCCTCTTTGACACATTTAGGGAAACTTCA
TTTGAGAAGGGGATCATGTAAAATGTGGACATGTTCAGCTACTCATGCTGACACATTAAGATACAAATCCTGGGG
CCGTACAGTTATTGGGACAACTGTACCCCATCCATTAGAAATGTTGGGTCCACAACATCGAAAAGAGACTCCTTGT
GCACCATGTAACACATCAGGGTTCAATTATGTTTCTGTGCATTGTCCAGACGGGATCCATGACGTCTTTAGTTCACG
GGGACCATTGCCTGCTTATCTAGGGTCTAAAACATCTGAATCTACATCTATTTTGCAGCCTTGGGAAAGGGAAAGC
AAAGTCCCACTGATTAAAAGAGCTACACGTCTTAGAGATGCTATCTCTTGGTTTGTTGAACCCGACTCTAAACTAGC

AATGACTATACTTTCTAACATCCACTCTTTAACAGGCGAAGAATGGACCAAAAGGCAGCATGGGTTCAAAAGAACA
GGGTCTGCCCTTCATAGGTTTTCGACATCTCGGATGAGCCATGGTGGGTTCGCATCTCAGAGCACTGCAGCATTGA
CCAGGTTGATGGCAACTACAGACACCATGAGGGATCTGGGAGATCAGAATTTCGACTTTTATTCCAAGCAACGTT
GCTCTATGCTCAAATTACCACCACTGTTGCAAGAGACGGATGGATCACCAGTTGTACAGATCATTATCATATTGCCT
GTAAGTCCTGTTTGAGACCCATAGAAGAGATCACCCTGGACTCAAGTATGGACTACACGCCCCCAGATGTATCCCA
TGTGCTGAAGACATGGAGGAATGGGGAAGGTTCGTGGGGACAAGAGATAAAACAGATCTATCCTTTAGAAGGGA
ATTGGAAGAAITTAGCACCTGCTGAGCAATCCTATCAAGTCGGCAGATGTATAGGTTTTCTATATGGAGACTTGGC
GTATAGAAAATCTACTCATGCCGAGGACAGTTCTCTATTTCCTCTATCTATACAAGGTCGTATTAGAGGTCGAGGTT
TCTTAAAAGGGTTGCTAGACGGATTAATGAGAGCAAGTTGCTGCCAAGTAATACACCGGAGAAGTCTGGCTCATT
TGAAGAGGCCGGCCAACGCAGTGTACGGAGGTTTGATTTACTTGATTGATAAATTGAGTGTATCACCTCCATTCCT
TTCTCTTACTAGATCAGGACCTATTAGAGACGAATTAGAAACGATTCCCCACAAGATCCCAACCTCCTATCCGACAA
GCAACCGTGATATGGGGGTGATTGTCAGAAATTACTTCAAATACCAATGCCGTCTAATTGAAAAGGGAAAATACA
GATCACATTATTCACAATTATGGTTATTCTCAGATGTCTTATCCATAGACTTCATTGGACCATTCTCTATTTCCACCAC
CCTCTTGCAAATCCTATACAAGCCATTTTTATCTGGGAAAGATAAGAATGAGTTGAGAGAGCTGGCAAATCTTTCTT
CATTGCTAAGATCAGGAGAGGGGTGGGAAGACATACATGTGAAATTCTTCACCAAGGACATATTATTGTGTCCAG
AGGAAATCAGACATGCTTGCAAGTTCGGGATTGCTAAGGATAATAATAAAGACATGAGCTATCCCCCTTGGGGAA
GGGAATCCAGAGGGACAATTACAACAATCCCTGTTTATTATACGACCACCCCTTACCCAAAGATGCTAGAGATGCC
TCCAAGAATCCAAAATCCCCTGCTGTCCGGAATCAGGTTGGGCCAATTACCAACTGGCGCTCATTATAAAATTCGG
AGTATATTACATGGAATGGGAATCCATTACAGGGACTTCTTGAGTTGTGGAGACGGCTCCGGAGGGATGACTGCT
GCATTACTACGAGAAAATGTGCATAGCAGAGGAATATTCAATAGTCTGTTAGAATTATCAGGGTCAGTCATGCGA
GGCGCCTCTCCTGAGCCCCCCAGTGCCCTAGAAACTTTAGGAGGAGATAAATCGAGATGTGTAAATGGTGAAACA
TGTTGGGAATATCCATCTGACTTATGTGACCCAAGGACTTGGGACTATTTCCTCCGACTCAAAGCAGGCTTGGGGC
TTCAAATTGATTTAATTGTAATGGATATGGAAGTTCGGGATTCTTCTACTAGCCTGAAAATTGAGACGAATGTTAG
AAATTATGTGCACCGGATTTTGGATGAGCAAGGAGTTTTAATCTACAAGACTTATGGAACATATATTTGTGAGAGC
GAAAAGAATGCAGTAACAATCCTTGGTCCCATGTTCAAGACGGTCGACTTAGTTCAAACAGAATTTAGTAGTTCTC
AAACGTCTGAAGTATATATGGTATGTAAAGGTTTGAAGAAATTAATCGATGAACCCAATCCCGATTGGTCTTCCAT
CAATGAATCCTGGAAAAACCTGTACGCATTCCAGTCATCAGAACAGGAATTTGCCAGAGCAAAGAAGGTTAGTAC
ATACTTTACCTTGACAGGTATTCCCTCCCAATTCATTCCTGATCCTTTTGTAAACATTGAGACTATGCTACAAATATT

*CGGAGTACCCACGGGTGTGTCTCATGCGGCTGCCTTAAAATCATCTGATAGACCTGCAGATTTATTGACCATTAGC*
*CTTTTTTATATGGCGATTATATCGTATTATAACATCAATCATATCAGAGTAGGACCGATACCTCCGAACCCCCCATC*
*AGATGGAATTGCACAAAATGTGGGGATCGCTATAACTGGTATAAGCTTTTGGCTGAGTTTGATGGAGAAAGACAT*
*TCCACTATATCAACAGTGTTTAGCAGTTATCCAGCAATCATTCCCGATTAGGTGGGAGGCTGTTTCAGTAAAAGGA*
*GGATACAAGCAGAAGTGGAGTACTAGAGGTGATGGCTCCCAAAAGATACCCGAATTTCAGACTCCTTGGCCCCA*
*ATCGGGAACTGGATCAGATCTCTGGAATTGGTCCGAAACCAAGTTCGTCTAAATCCATTCAATGAGATCTTGTTCA*
*ATCAGCTATGTCGTACAGTGGATAATCATTTGAAATGGTCAAATTTGCGAAGAAACACAGGAATGTTGAATGGA*
*TCAATAGACGAATTTCAAAAGAAGACCGGTCTATACTGAGTTGAAGAGTGACCTACACGAGAAAACTCTTGGA*
*GAGATTAA*AAAATCATGAGGAGACTCCAAACTTTAAGTATGAAAAAAACTTTGATCCTTAAGACCCTCTTGTGGT
TTTTATTTTTTATCTGGTTTTGTGGTCTTC

3' Leader sequence

5' Trailer sequence

Bold sequence : Intergenic region (IGR)

*ACGCGTATCATTCTGTTTCGTCACT* IGR(upstream of Morrenton G gene)

*GAAAGCTTCATTGCTGCAGATGACAACCACACTCACCAAAG* IGR( Dowstream of Morreton G gene)

FIG. 2

|  | Mock | VSVwt | MorVwt | VSV MorV G |
|---|---|---|---|---|
| MIA CA CaPa-2 | | | | |
| Hs766T | | | | |
| CFPAC-1 | | | | |
| BxPC-3 | | | | |

*Mouse Pancreatic Center Cell line*

|  | | | | |
|---|---|---|---|---|
| 6606PDA | | | | |
| Pan02 | | | | |

SEQUENCE LISTING

<160> NUMBER OF SEQ ID NOS: 3

<210> SEQ ID NO 1
<211> LENGTH: 25
<212> TYPE: DNA
<213> ORGANISM: Morreton virus

<400> SEQUENCE: 1
acgcgtatca ttctgtttcg tcact 25

<210> SEQ ID NO 2
<211> LENGTH: 41
<212> TYPE: DNA
<213> ORGANISM: Morreton virus

<400> SEQUENCE: 2
gaaagcttca ttgctgcaga tgacaaccac actcaccaaa g 41

<210> SEQ ID NO 3
<211> LENGTH: 11185
<212> TYPE: DNA
<213> ORGANISM: Artificial Sequence
<220> FEATURE:
<223> OTHER INFORMATION: Genome sequence of chimeric VSV-MorV-G virus
<220> FEATURE:
<221> NAME/KEY: misc_feature
<222> LOCATION: (4509)..(4509)
<223> OTHER INFORMATION: n is a, c, g, or t

<400> SEQUENCE: 3
atcattaaaa ggctcaggag aaactttaac agtaatcaaa atgtctgtta cagtcaagag 60
aatcattgac aacacagtcg tagttccaaa acttcctgca aatgaggatc cagtggaata 120
cccggcagat tacttcagaa aatcaaagga gattcctctt tacatcaata ctacaaaaag 180
tttgtcagat ctaagaggat atgtctacca aggcctcaaa tccggaaatg tatcaatcat 240
acatgtcaac agctacttgt atggagcatt aaaggacatc cggggtaagt tggataaaga 300
ttggtcaagt ttcggaataa acatcgggaa agcaggggat acaatcggaa tatttgacct 360
tgtatccttg aaagccctgg acggcgtact tccagatgga gtatcggatg cttccagaac 420
cagcgcagat gacaaatggt tgcctttgta tctacttggc ttatacagag tgggcagaac 480
acaaatgcct gaatacagaa aaaagctcat ggatgggctg acaaatcaat gcaaaatgat 540
caatgaacag tttgaacctc ttgtgccaga aggtcgtgac atttttgatg tgtggggaaa 600
tgacagtaat tacacaaaaa ttgtcgctgc agtggacatg ttcttccaca tgttcaaaaa 660
acatgaatgt gcctcgttca gatacggaac tattgtttcc agattcaaag attgtgctgc 720
attggcaaca tttggacacc tctgcaaaat aaccggaatg tctacagaag atgtaacgac 780
ctggatcttg aaccgagaag ttgcagatga aatggtccaa atgatgcttc caggccaaga 840
aattgacaag gccgattcat acatgcctta tttgatcgac tttggattgt cttctaagtc 900
tccatattct tccgtcaaaa accctgcctt ccacttctgg gggcaattga cagctcttct 960
gctcagatcc accagagcaa ggaatgcccg acagcctgat gacattgagt atacatctct 1020
tactacagca ggtttgttgt acgcttatgc agtaggatcc tctgccgact tggcacaaca 1080
gttttgtgtt ggagataaca aatacactcc agatgatagt accggaggat tgacgactaa 1140
tgcaccgcca caaggcagag atgtggtcga atggctcgga tggtttgaag atcaaaacag 1200
aaaaccgact cctgatatga tgcagtatgc gaaaagagca gtcatgtcac tgcaaggcct 1260
aagagagaag acaattggca agtatgctaa gtcagaattt gacaaatgac cctataattc 1320

-continued

```
tcagatcacc tattatatat tatgctacat atgaaaaaaa ctaacagata tcatggataa   1380
tctcacaaaa gttcgtgagt atctcaagtc ctattctcgt ctggatcagg cggtaggaga   1440
gatagatgag atcgaagcac aacgagctga aaagtccaat tatgagttgt tccaagagga   1500
tggagtggaa gagcatacta agccctctta ttttcaggca gcagatgatt ctgacacaga   1560
atctgaacca gaaattgaag acaatcaagg cttgtatgca ccagatccag aagctgagca   1620
agttgaaggc tttatacagg ggcctttaga tgactatgca gatgaggaag tggatgttgt   1680
atttacttcg gactggaaac agcctgagct tgaatctgac gagcatggaa agaccttacg   1740
gttgacatcg ccagagggtt taagtggaga gcagaaatcc cagtggcttt cgacgattaa   1800
agcagtcgtg caaagtgcca aatactggaa tctggcagag tgcacatttg aagcatcggg   1860
agaaggggtc attatgaagg agcgccagat aactccggat gtatataagg tcactccagt   1920
gatgaacaca catccgtccc aatcagaagc agtatcagat gtttggtctc tctcaaagac   1980
atccatgact ttccaaccca agaaagcaag tcttcagcct ctcaccatat ccttggatga   2040
attgttctca tctagaggag agttcatctc tgtcggaggt gacggacgaa tgtctcataa   2100
agaggccatc ctgctcggcc tgagatacaa aaagttgtac aatcaggcga gagtcaaata   2160
ttctctgtag actatgaaaa aaagtaacag atatcacgat ctaagtgtta tcccaatcca   2220
ttcatcatga gttccttaaa gaagattctc ggtctgaagg ggaaaggtaa gaaatctaag   2280
aaattaggga tcgcaccacc cccttatgaa gaggacacta gcatggagta tgctccgagc   2340
gctccaattg acaaatccta ttttggagtt gacgagatgg acacctatga tccgaatcaa   2400
ttaagatatg agaaattctt ctttacagtg aaaatgacgg ttagatctaa tcgtccgttc   2460
agaacatact cagatgtggc agccgctgta tcccattggg atcacatgta catcggaatg   2520
gcagggaaac gtcccttcta caaaatcttg gctttttttgg gttcttctaa tctaaaggcc   2580
actccagcgg tattggcaga tcaaggtcaa ccagagtatc acgctcactg cgaaggcagg   2640
gcttatttgc cacataggat ggggaagacc cctcccatgc tcaatgtacc agagcacttc   2700
agaagaccat tcaatatagg tctttacaag ggaacgattg agctcacaat gaccatctac   2760
gatgatgagt cactggaagc agctcctatg atctgggatc atttcaattc ttccaaattt   2820
tctgatttca gagagaaggc cttaatgttt ggcctgattg tcgagaaaaa ggcatctgga   2880
gcgtgggtcc tggactctat cggccacttc aaatgagcta gtctaacttc tagcttctga   2940
acaatccccg gtttactcag tctcccctaa ttccagcctc tcgaacaact aatatcctgt   3000
cttttctatc cctatgaaaa aaactaacag agatcgatct gtttacgcgt atcattctgt   3060
ttcgtcacta tgctggtttt atacctgtta ttgagccttt tggctctggg agctcaatgc   3120
aagttcacta tagtatttcc tcacaatcaa aaagggaatt ggaaaaatgt aaggcaaatt   3180
atcagtattg tccttctagt tctgacttga attggcacaa tgggctgatt ggcacttctc   3240
tccaagtcaa aatgcccaaa agccataagg ccatccaagc ggatggttgg atgtgtcatg   3300
ctgccaagtg ggtgactact tgtgacttca gatggtacgg acctaaatat gtgacacatt   3360
ctataaagtc catgatacct acagtcgacc agtgtaaaga aagtatagcc cagactaaac   3420
aaggaacgtg gttaaatccg ggtttccctc cccaaagttg tggatatgct tccgttacag   3480
atgcagaggc tgtgatagtc aaagcaaccc cccaccaggt tttggttgac gaatatacag   3540
gagaatgggt tgactcccaa tttccgactg gaaaatgcaa taaagacatt tgcccaacag   3600
ttcacaactc aactacctgg cactcagatt ataaggtcac tggcctttgc gatgcaaatt   3660
```

-continued

```
tgatctcaat ggacatcact ttcttctccg aagatggaaa attaacatcc ctcgggaaag   3720
aaggaacagg gttcagaagc aattactttg catacgaaaa tggtgacaaa gcatgccgca   3780
tgcagtactg taaacactgg ggagttcgac ttccatccgg agtgtggttc gaaatggcag   3840
ataaagacat ctataatgat gcgaaattcc cggattgccc tgaaggatca tccattgcgg   3900
ctccctctca gacttcagtc gatgttagtc tcattcagga tgtagagaga atcttggact   3960
actctttgtg tcaggaaacc tggagcaaaa ttcgtgctca tttgcccatt tcaccagttg   4020
acctcagcta tttatcccca aaaaatcctg gaactggtcc tgcattcact atcatcaatg   4080
ggacattaaa atactttgag actcgataca taagagtcga tatcgcagga cccatcattc   4140
ctcaaatgag aggagtaatc agcggaacca cgaccgagag agagctgtgg acggactggt   4200
acccctacga agatgttgaa atcggaccaa atggggtttt gaaaactgct acagggtata   4260
agttcccttt atacatgatt ggccacggca tgctcgactc agatctccac atctcatcaa   4320
aggctcaggt tttgaacat ccccatattc aggatgctgc ttctcagctt cctgatgatg   4380
agactttatt ttttggtgat actggactct cgaaaaaccc catagagctt gtagaaggtt   4440
ggttcagcgg atggaaaagc actattgctt tctttttct tcataatagg gcttgtgatc   4500
ggattatant tggttcttag gattggaatc gctttatgca tcaaatgccg agtgcaggag   4560
aaaaggccca aaatttacac tgatgtggaa atgaacagat tggatcgatg aaagcttcat   4620
tgctgcagat gacaaccaca ctcaccaaag gctagccaga ttcttcatgt ttggaccaaa   4680
tcaacttgtg ataccatgct caaagaggcc tcaattatat ttgagttttt aatttttatg   4740
aaaaaaacta acagcaatca tggaagtcca cgattttgag accgacgagt tcaatgattt   4800
caatgaagat gactatgcca caagagaatt cctgaatccc gatgagcgca tgacgtactt   4860
gaatcatgct gattacaacc tgaattctcc tctaattagt gatgatattg acaatttaat   4920
caggaaattc aattctcttc caattccctc gatgtgggat agtaagaact gggatggagt   4980
tcttgagatg ttaacgtcat gtcaagccaa tcccatccca acatctcaga tgcataaatg   5040
gatgggaagt tggttaatgt ctgataatca tgatgccagt caagggtata gtttttaca   5100
tgaagtggac aaagaggcag aaataacatt tgacgtggtg gagaccttca tccgcggctg   5160
gggcaacaaa ccaattgaat acatcaaaaa ggaaagatgg actgactcat tcaaaattct   5220
cgcttatttg tgtcaaaagt ttttggactt acacaagttg acattaatct taaatgctgt   5280
ctctgaggtg gaattgctca acttggcgag gactttcaaa ggcaaagtca gaagaagttc   5340
tcatggaacg aacatatgca ggattagggt tcccagcttg ggtcctactt ttatttcaga   5400
aggatgggct tacttcaaga aacttgatat tctaatggac cgaaactttc tgttaatggt   5460
caaagatgtg attataggga ggatgcaaac ggtgctatcc atggtatgta gaatagacaa   5520
cctgttctca gagcaagaca tcttctccct tctaaatatc tacagaattg gagataaaat   5580
tgtggagagg cagggaaatt tttcttatga cttgattaaa atggtggaac cgatatgcaa   5640
cttgaagctg atgaaattag caagagaatc aaggccttta gtcccacaat tccctcattt   5700
tgaaaatcat atcaagactt ctgttgatga aggggcaaaa attgaccgag gtataagatt   5760
cctccatgat cagataatga gtgtgaaaac agtggatctc acactggtga tttatggatc   5820
gttcagacat tggggtcatc cttttataga ttattacact ggactagaaa aattacattc   5880
ccaagtaacc atgaagaaag atattgatgt gtcatatgca aaagcacttg caagtgattt   5940
agctcggatt gttctatttc aacagttcaa tgatcataaa aagtggttcg tgaatggaga   6000
cttgctccct catgatcatc cctttaaaag tcatgttaaa gaaaatacat ggcccacagc   6060
```

-continued

```
tgctcaagtt caagattttg gagataaatg gcatgaactt ccgctgatta aatgttttga   6120
aatacccgac ttactagacc catcgataat atactctgac aaaagtcatt caatgaatag   6180
gtcagaggtg ttgaaacatg tccgaatgaa tccgaacact cctatcccta gtaaaaaggt   6240
gttgcagact atgttggaca caaaggctac caattggaaa gaatttctta aagagattga   6300
tgagaagggc ttagatgatg atgatctaat tattggtctt aaaggaaagg agagggaact   6360
gaagttggca ggtagatttt tctccctaat gtcttggaaa ttgcgagaat actttgtaat   6420
taccgaatat ttgataaaga ctcatttcgt ccctatgttt aaaggcctga caatggcgga   6480
cgatctaact gcagtcatta aaaagatgtt agattcctca tccggccaag gattgaagtc   6540
atatgaggca atttgcatag ccaatcacat tgattacgaa aaatggaata accaccaaag   6600
gaagttatca aacggcccag tgttccgagt tatgggccag ttcttaggtt atccatcctt   6660
aatcgagaga actcatgaat tttttgagaa aagtcttata tactacaatg gaagaccaga   6720
cttgatgcgt gttcacaaca acacactgat caattcaacc tcccaacgag tttgttggca   6780
aggacaagag ggtggactgg aaggtctacg gcaaaaagga tggagtatcc tcaatctact   6840
ggttattcaa agagaggcta aaatcagaaa cactgctgtc aaagtcttgg cacaaggtga   6900
taatcaagtt atttgcacac agtataaaac gaagaaatcg agaaacgttg tagaattaca   6960
gggtgctctc aatcaaatgg tttctaataa tgagaaaatt atgactgcaa tcaaaatagg   7020
gacagggaag ttaggacttt tgataaatga cgatgagact atgcaatctg cagattactt   7080
gaattatgga aaaataccga ttttccgtgg agtgattaga gggttagaga ccaagagatg   7140
gtcacgagtg acttgtgtca ccaatgacca aatacccact tgtgctaata taatgagctc   7200
agtttccaca aatgctctca ccgtagctca ttttgctgag aacccaatca atgccatgat   7260
acagtacaat tattttggga catttgctag actcttgttg atgatgcatg atcctgctct   7320
tcgtcaatca ttgtatgaag ttcaagataa gataccgggc ttgcacagtt ctactttcaa   7380
atacgccatg ttgtatttgg acccttccat tggaggagtg tcgggcatgt ctttgtccag   7440
gtttttgatt agagccttcc cagatcccgt aacagaaagt ctctcattct ggagattcat   7500
ccatgtacat gctcgaagtg agcatctgaa ggagatgagt gcagtatttg gaaaccccga   7560
gatagccaag tttcgaataa ctcacataga caagctagta gaagatccaa cctctctgaa   7620
catcgctatg ggaatgagtc cagcgaactt gttaaagact gaggttaaaa aatgcttaat   7680
cgaatcaaga caaaccatca ggaaccaggt gattaaggat gcaaccatat atttgtatca   7740
tgaagaggat cggctcagaa gtttcttatg gtcaataaat cctctgttcc ctagattttt   7800
aagtgaattc aaatcaggca ctttttttggg agtcgcagac gggctcatca gtctatttca   7860
aaattctcgt actattcgga actcctttaa gaaaaagtat catagggaat tggatgattt   7920
gattgtgagg agtgaggtat cctctttgac acatttaggg aaacttcatt tgagaagggg   7980
atcatgtaaa atgtggacat gttcagctac tcatgctgac acattaagat acaaatcctg   8040
gggccgtaca gttattggga caactgtacc ccatccatta gaaatgttgg gtccacaaca   8100
tcgaaaagag actccttgtg caccatgtaa cacatcaggg ttcaattatg tttctgtgca   8160
ttgtccagac gggatccatg acgtctttag ttcacgggga ccattgcctg cttatctagg   8220
gtctaaaaca tctgaatcta catctatttt gcagccttgg gaaagggaaa gcaaagtccc   8280
actgattaaa agagctacac gtcttagaga tgctatctct tggtttgttg aacccgactc   8340
taaactagca atgactatac tttctaacat ccactcttta acaggcgaag aatggaccaa   8400
```

-continued

```
aaggcagcat gggttcaaaa gaacagggtc tgcccttcat aggttttcga catctcggat   8460
gagccatggt gggttcgcat ctcagagcac tgcagcattg accaggttga tggcaactac   8520
agacaccatg agggatctgg gagatcagaa tttcgacttt ttattccaag caacgttgct   8580
ctatgctcaa attaccacca ctgttgcaag agacggatgg atcaccagtt gtacagatca   8640
ttatcatatt gcctgtaagt cctgtttgag acccatagaa gagatcaccc tggactcaag   8700
tatggactac acgcccccag atgtatccca tgtgctgaag acatggagga atggggaagg   8760
ttcgtgggga caagagataa aacagatcta tcctttagaa gggaattgga agaatttagc   8820
acctgctgag caatcctatc aagtcggcag atgtataggt tttctatatg gagacttggc   8880
gtatagaaaa tctactcatg ccgaggacag ttctctattt cctctatcta tacaaggtcg   8940
tattagaggt cgaggtttct taaaagggtt gctagacgga ttaatgagag caagttgctg   9000
ccaagtaata caccggagaa gtctggctca tttgaagagg ccggccaacg cagtgtacgg   9060
aggtttgatt tacttgattg ataaattgag tgtatcacct ccattccttt ctcttactag   9120
atcaggacct attagagacg aattagaaac gattccccac aagatcccaa cctcctatcc   9180
gacaagcaac cgtgatatgg gggtgattgt cagaaattac ttcaaatacc aatgccgtct   9240
aattgaaaag ggaaaataca gatcacatta ttcacaatta tggttattct cagatgtctt   9300
atccatagac ttcattggac cattctctat ttccaccacc ctcttgcaaa tcctatacaa   9360
gccattttta tctgggaaag ataagaatga gttgagagag ctggcaaatc tttcttcatt   9420
gctaagatca ggagaggggt gggaagacat acatgtgaaa ttcttcacca aggacatatt   9480
attgtgtcca gaggaaatca gacatgcttg caagttcggg attgctaagg ataataataa   9540
agacatgagc tatcccccctt ggggaaggga atccagaggg acaattacaa caatccctgt   9600
ttattatacg accacccctt acccaaagat gctagagatg cctccaagaa tccaaaatcc   9660
cctgctgtcc ggaatcaggt tggccaatt accaactggc gctcattata aaattcggag   9720
tatattacat ggaatgggaa tccattacag ggacttcttg agttgtggag acggctccgg   9780
agggatgact gctgcattac tacgagaaaa tgtgcatagc agaggaatat tcaatagtct   9840
gttagaatta tcagggtcag tcatgcgagg cgcctctcct gagcccccca gtgccctaga   9900
aactttagga ggagataaat cgagatgtgt aaatggtgaa acatgttggg aatatccatc   9960
tgacttatgt gacccaagga cttgggacta tttcctccga ctcaaagcag gcttggggct  10020
tcaaattgat ttaattgtaa tggatatgga agttcgggat tcttctacta gcctgaaaat  10080
tgagacgaat gttagaaatt atgtgcaccg gattttggat gagcaaggag ttttaatcta  10140
caagacttat ggaacatata tttgtgagag cgaaaagaat gcagtaacaa tccttggtcc  10200
catgttcaag acggtcgact tagttcaaac agaatttagt agttctcaaa cgtctgaagt  10260
atatatggta tgtaaaggtt tgaagaaatt aatcgatgaa cccaatcccg attggtcttc  10320
catcaatgaa tcctggaaaa acctgtacgc attccagtca tcagaacagg aatttgccag  10380
agcaaagaag gttagtacat actttacctt gacaggtatt ccctcccaat tcattcctga  10440
tccttttgta aacattgaga ctatgctaca aatattcgga gtacccacgg gtgtgtctca  10500
tgcggctgcc ttaaaatcat ctgatagacc tgcagattta ttgaccatta gccttttta  10560
tatggcgatt atatcgtatt ataacatcaa tcatatcaga gtaggaccga tacctccgaa  10620
ccccccatca gatggaattg cacaaaatgt ggggatcgct ataactggta taagcttttg  10680
gctgagtttg atggagaaag acattccact atatcaacag tgtttagcag ttatccagca  10740
atcattcccg attaggtggg aggctgtttc agtaaaagga ggatacaagc agaagtggag  10800
```

-continued

```
tactagaggt gatgggctcc caaaagatac ccgaatttca gactccttgg ccccaatcgg  10860

gaactggatc agatctctgg aattggtccg aaaccaagtt cgtctaaatc cattcaatga  10920

gatcttgttc aatcagctat gtcgtacagt ggataatcat ttgaaatggt caaatttgcg  10980

aagaaacaca ggaatgattg aatggatcaa tagacgaatt tcaaaagaag accggtctat  11040

actgatgttg aagagtgacc tacacgagga aaactcttgg agagattaaa aaatcatgag  11100

gagactccaa actttaagta tgaaaaaaac tttgatcctt aagaccctct tgtggtttta  11160

ttttttatct ggttttgtgg tcttc                                        11185
```

CHIMERIC VESICULOVIRUSES AND METHODS OF USE

CROSS-REFERENCE TO RELATED APPLICATIONS

This application is a National Stage application under 35 U.S.C. § 371 of International Application No. PCT/US2020/046503, having an International Filing Date of Aug. 14, 2020, which claims the benefit of U.S. Patent Application Ser. No. 62/887,991, filed on Aug. 16, 2019. The disclosure of the prior application is considered part of (and is incorporated by reference in) the disclosure of this application.

SEQUENCE LISTING

This document contains a sequence listing that has been submitted electronically as an ASCII text file. The ASCII text file, created on Sep. 15, 2020, is 15,427 bytes in size. The material in the ASCII text file is hereby incorporated by reference in its entirety.

STATEMENT REGARDING FEDERAL FUNDING

This invention was made with government support under CA195764 awarded by the National Institutes of Health. The government has certain rights in the invention.

BACKGROUND

1. Technical Field

This document relates to methods and materials for treating cancer. For example, this document provides chimeric vesiculoviruses (e.g., chimeric vesicular stomatitis viruses (VSVs)) and methods for using such chimeric vesiculoviruses as an oncolytic agent (e.g., to treat cancer).

2. Background Information

Despite vast efforts, cancer remains a major public health issue in the United States with over 1.6 million new cases in 2017 alone (National Cancer Institute, "Cancer Stat Facts: Cancer of Any Site," seer.cancer.gov/statfacts/html/all.html). Traditional therapies, such as chemotherapeutics, radiation therapy and surgery, often fail, especially when cancer is advanced. Oncolytic virotherapy can provide an alternative approach to cancer treatment by utilizing selectively replicating viruses to destroy tumors, activate adaptive immune responses, and ensure a life-long immunity against the tumors (Russell et al., 2017 *Molecular Therapy* 25:1107-1116).

SUMMARY

VSV is a negative-sense RNA Vesiculovirus of the family Rhabdoviridae with broad mammalian cellular tropism, fast lytic cycle, and high sensitivity to host IFN associated antiviral active immunity (Bishnoi et al., *Viruses* 10, doi: 10.3390/v10020090 (2018); and Sharif-Askari et al., *Virology* 365:20-33 (2007)). Wild type VSV (VSVwt) can cause lethal neurotoxicity and liver toxicity in laboratory rodents (Ahmed et al., *J Virol* 77(8):4646-4657 (2003); Muik et al., *Cancer Res* 74:3567-3578 (2014); Naik et al., *Cancer Gene Ther* 19:443-450 (2012); Johnson et al., *Virology* 360:36-49 (2007); and Zhang et al., *Hum Gene Ther Clin Dev* 27:111-122 (2016)). In addition, there are reported cases of VSV-induced encephalitis in humans (Quiroz et al., *Am J Trop Med Hyg* 39:312-314 (1988)). As described herein, chimeric vesiculoviruses can be used as a retroviral platform for safe and effective oncolytic virotherapy.

This document provides methods and materials for treating cancer. For example, this document provides chimeric vesiculoviruses (e.g., chimeric VSVs) having oncolytic anti-cancer activity. In some cases, one or more chimeric vesiculoviruses described herein (e.g., one or more chimeric vesiculoviruses having oncolytic anti-cancer activity) can be used as an oncolytic agent (e.g., to treat cancer). For example, one or more chimeric vesiculoviruses described herein can be administered to a mammal having cancer to treat that mammal.

As described herein, a chimeric VSV engineered in a manner (a) to express nucleic acid encoding a G polypeptide (e.g., a G gene) of a morreton virus (MorV) and (b) to not express nucleic acid encoding a G polypeptide (e.g., a G gene) of a VSV genome can maintain the fast lytic cycle of VSV and can demonstrate the potent cancer cell-specific cytotoxic effects of MorV. In some cases, a chimeric VSV engineered to express nucleic acid encoding a G polypeptide of a MorV and engineered to not express nucleic acid encoding a G polypeptide of a VSV genome can be a chimeric VSV where nucleic acid encoding a G polypeptide of a VSV genome is replaced with nucleic acid encoding a G polypeptide of a MorV. Such a chimeric VSV can be referred to herein as VSV-MorV-G Also as demonstrated herein, VSV-MorV-G can be resistant to VSV neutralizing antibodies and can induce oncolysis in cancer cells. Accordingly, chimeric vesiculoviruses described herein (e.g., VSV-MorV-G) can be used as anticancer agents to reduce the number of cancer cells within a mammal (e.g., a human).

In general, one aspect of this document features chimeric vesiculoviruses. A chimeric vesiculovirus can include, or consist essentially of, (a) a first genomic fragment of a first vesiculovirus species; and (b) a second genomic fragment of a second vesiculovirus species different from said first vesiculovirus species. The first vesiculovirus species can be a VSV. The second vesiculovirus species can be a MorV. The first genomic fragment of the first vesiculovirus species can include nucleic acid encoding a N polypeptide, nucleic acid encoding a P polypeptide, nucleic acid encoding a M polypeptide, and nucleic acid encoding a L polypeptide. The second genomic fragment of the second vesiculovirus species can include nucleic acid encoding a G polypeptide. The nucleic acid encoding a G polypeptide also can include a 3' intergenic region (IGR) and a 5' IGR. The 3' IGR can include 24 or 25 nucleotides. The 3' IGR can include a nucleotide sequence as set forth in SEQ ID NO:1. The 5' IGR can include 40 or 41 nucleotides. The 5' IGR can include a nucleotide sequence as set forth in SEQ ID NO:2. The chimeric vesiculovirus can include a nucleotide sequence having at least 80% sequence identity to a nucleotide sequence set forth in SEQ ID NO:3. For example, the chimeric vesiculovirus can include the nucleotide sequence set forth in SEQ ID NO:3.

In another aspect, this document features methods for treating a mammal having cancer. The methods can include, or consist essentially of, administering, to a mammal having cancer, a chimeric vesiculovirus having oncolytic anti-cancer activity, where the chimeric vesiculovirus includes (a) a first genomic fragment of a first vesiculovirus species and (b) a second genomic fragment of a second vesiculovirus species different from the first vesiculovirus species. The mammal can be a human. The cancer can be selected from the group consisting of, hepatobiliary cancer, pancreatic cancer, glioblastoma, leukemia, lymphoma, or myeloma. The first vesiculovirus species can be a VSV. The second vesiculovirus species can be a MorV. The first genomic fragment of the first vesiculovirus species can include nucleic acid encoding a N polypeptide, nucleic acid encoding a P polypeptide, nucleic acid encoding a M polypeptide, and nucleic acid encoding a L polypeptide. The second genomic fragment of the second vesiculovirus species can include nucleic acid encoding a G polypeptide. The nucleic acid encoding a G polypeptide also can include a 3' IGR and a 5' IGR. The 3' IGR can include 24 or 25 nucleotides. The 3' IGR can include a nucleotide sequence as set forth in SEQ ID NO:1. The 5' IGR can include 40 nucleotides or 41 nucleotides. The 5' IGR can include a nucleotide sequence as set forth in SEQ ID NO:2. The chimeric vesiculovirus can include a nucleotide sequence having at least 80% sequence identity to the nucleotide sequence set forth in SEQ ID NO:3. For example, the chimeric vesiculovirus can include the nucleotide sequence set forth in SEQ ID NO:3.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2. Complete genome sequence of an exemplary VSV-MorV-G (SEQ ID NO:3). The nucleotides are shown from the 3' end to the 5'end (antisense genome) include 5 major genes: VSV N, VSV M, VSV P, MorV G and its IGRs, and VSV L.

DETAILED DESCRIPTION

Figure 1:
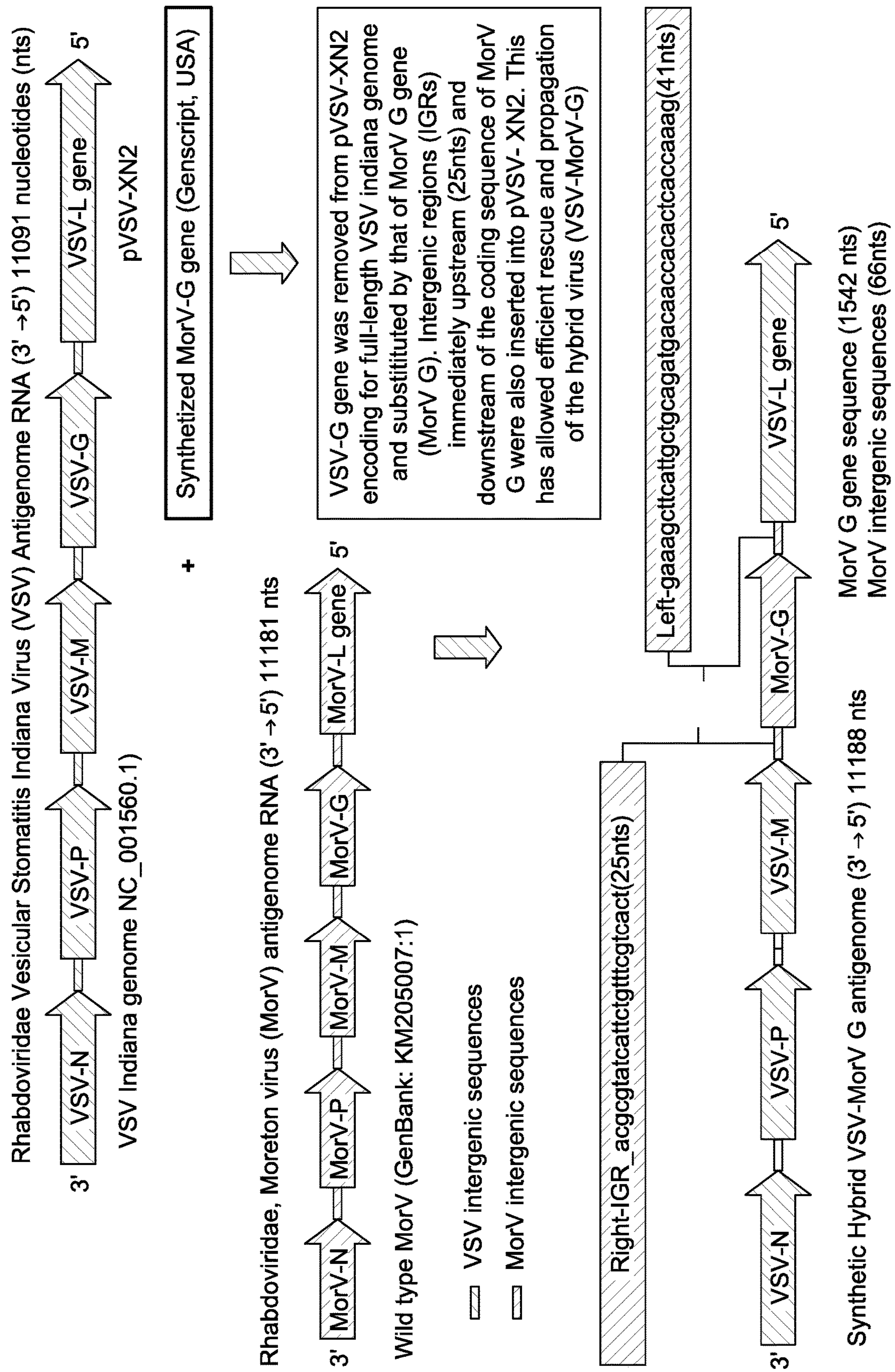
FIG. 1. Schematic exemplary genomes of VSV, MorV, and VSV-MorV-G according to some embodiments. Intergenic regions (IGRs) shown include a MorV-G right IGR (SEQ ID NO:1) and a MorV-G left IGR (SEQ ID NO:2)

This document provides methods and materials for treating cancer. For example, this document provides methods and materials for treating cancer using one or more chimeric vesiculoviruses described herein (e.g., one or more chimeric vesiculoviruses having oncolytic activity such as a VSV-MorV-G) as an oncolytic agent (e.g., to treat cancer). In some cases, this document provides chimeric vesiculoviruses having oncolytic anti-cancer activity. For example, this document provides chimeric vesiculoviruses containing a VSV genome that does not express nucleic acid encoding a G polypeptide of VSV and that does express nucleic acid encoding a G polypeptide of a MorV. Such chimeric vesiculoviruses can have oncolytic anti-cancer activity. In some cases, this document provides methods for using one or more chimeric vesiculoviruses provided herein (e.g., a VSV-MorV-G) to treat a mammal having cancer. For example, one or more chimeric vesiculoviruses described herein can be administered to a mammal (e.g., a human) having cancer to reduce the number of cancer cells (e.g., by infecting and killing cancer cells) in that mammal. In some cases, one or more chimeric vesiculoviruses described herein can be administered to a mammal (e.g., a human) having cancer to stimulate anti-cancer immune responses in that mammal.

In some cases, a chimeric vesiculovirus provided herein (e.g., chimeric vesiculoviruses having oncolytic activity such as VSV-MorV-G) can be replication competent, can infect dividing cells (e.g., can infect only dividing cells), can be non-pathogenic (e.g., to a mammal being treated as described herein), can be non-neurotropic (e.g., to a mammal being treated as described herein), can bud through the endoplasmic reticulum, or any combination thereof. For example, a chimeric vesiculovirus provided herein (e.g., a VSV-MorV-G) can be replication competent, can infect dividing cells (e.g., can infect only dividing cells), can be non-pathogenic (e.g., to a mammal being treated as described herein), can be non-neurotropic (e.g., to a mammal being treated as described herein), and can bud through the endoplasmic reticulum.

In some cases, a chimeric vesiculovirus provided herein (e.g., a VSV-MorV-G) can bind to a cellular receptor (e.g., to facilitate viral entry to a cell). For example, a chimeric vesiculovirus described herein can bind to a low-density lipoprotein (LDL) receptor.

In some cases, a chimeric vesiculovirus provided herein (e.g., a VSV-MorV-G) can have reduced or eliminated neurotoxicity (e.g., as compared to a wild type vesiculovirus), can have reduced or eliminated hepatotoxicity (e.g., as compared to a wild type vesiculovirus), can have an increased oncolytic anti-cancer activity efficacy (e.g., as compared to a wild type vesiculovirus), or any combination thereof. For example, a chimeric vesiculovirus provided herein (e.g., a VSV-MorV-G) can have reduced or eliminated neurotoxicity (e.g., as compared to a wild type vesiculovirus), can have reduced or eliminated hepatotoxicity (e.g., as compared to a wild type vesiculovirus), and can have an increased oncolytic anti-cancer activity efficacy (e.g., as compared to a wild type vesiculovirus).

In some cases, a chimeric vesiculovirus provided herein (e.g., a VSV-MorV-G) may not be recognized (e.g., recognized and inactivated) by a vesiculovirus neutralizing antibody (e.g., as compared to a wild type vesiculovirus). For example, a chimeric VSV described herein may not be neutralized by a VSV neutralizing antibody present in a mammal having a pre-existing adaptive immunity to VSV.

Chimeric vesiculoviruses described herein (e.g., a VSV-MorV-G) can be any appropriate size. In some cases, a chimeric vesiculovirus described herein can be from about 90 nanometers (nm) to about 200 nm in length (e.g., across its longest dimension). For example, a chimeric vesiculovirus described herein can be about 100 nm in length (e.g., across its longest dimension).

Any appropriate vesiculovirus nucleic acid sequences can be used to create a chimeric vesiculovirus provided herein. For example, a VSV genome can be obtained and modified to include a nucleic acid sequence from a vesiculovirus that is different from VSV (e.g., MorV) for use in forming a chimeric vesiculovirus. In such an example, the VSV nucleic acid sequence encoding a VSV G polypeptide can be replaced with MorV nucleic acid encoding a MorV G polypeptide. Examples of different types of vesiculoviruses that can be used to make chimeric vesiculoviruses provided herein include, without limitation, VSV, MorV, Malpais Spring Virus, Perinet Virus (PERV), Radi Virus (RADIV), Jurona Virus (JURV), Yug Bogdanovac Virus (YBV), Carajas Virus (CRJV), Isfahan Virus, Cocal Virus (COCV), Ekpoma 1 virus, Ekpoma 2 virus, and Farmington Virus (FRMV).

In some cases, a genome of a first strain of one type of vesiculovirus can be obtained and modified to include a nucleic acid sequence from a second strain of the same type that is different from the first strain for use in forming a chimeric vesiculovirus. For example, a VSV genome of a first VSV strain can be obtained and modified to include a nucleic acid sequence from a second VSV strain that is different from the first VSV strain for use in forming a chimeric vesiculovirus. In such an example, a first strain of VSV nucleic acid sequence encoding a G polypeptide of a VSV strain (e.g., VSV strain Indiana) can be replaced with nucleic acid encoding a G polypeptide of second VSV strain (e.g., VSV strain New Jersey). Examples of different types of VSV strains that can be used to make chimeric vesiculoviruses provided herein include, without limitation, VSV strain Indiana, and VSV strain New Jersey. In some cases, a chimeric vesiculovirus provided herein can include one or more nucleotide sequences that do not naturally occur in a vesiculovirus. Nucleotide sequences that do not naturally occur in a vesiculovirus that can be engineered into a vesiculovirus can be from any appropriate source. In some cases, a nucleotide sequence that does not naturally occur in a vesiculovirus can be from a non-viral organism. In some cases, a nucleotide sequence that does not naturally occur in a vesiculovirus can be from a virus other than a vesiculovirus. Examples of nucleic acids that can be included in a chimeric vesiculovirus provided herein (e.g., a VSV-MorV-G) include, without limitation, nucleic acid encoding a nucleoprotein (a N polypeptide), nucleic acid encoding a phosphoprotein (a P polypeptide), nucleic acid encoding a matrix protein (a M polypeptide), nucleic acid encoding a glycoprotein (a G polypeptide), nucleic acid encoding a large protein (a L polypeptide), and the intergenic regions (IGRs) between nucleic acids that encode a polypeptide. In some cases, at least one of these nucleic acids can be maintained within the genome of a chimeric vesiculovirus provided herein and at least one of these nucleic acids can be replaced with nucleic acid from a different type of vesiculovirus or a different strain of vesiculovirus. For example, a chimeric vesiculovirus provided herein can be designed to maintain all the VSV nucleic acid of VSV except that the VSV nucleic acid encoding a G polypeptide is replaced with nucleic acid of a MorV encoding a MorV G polypeptide. Examples of chimeric vesiculovirus genomes are shown in FIG. 1.

In some cases, a chimeric vesiculovirus provided herein can include genomic fragments from two or more (e.g., two, three, four, five, or more) different vesiculovirus genomes. For example, a chimeric vesiculovirus provided herein can include a first genomic fragment (e.g., one or more nucleic acids encoding a polypeptide (or fragments thereof)) from a first type (e.g., a VSV) or strain (e.g., a VSV Indiana) of vesiculovirus and a second genomic fragment (e.g., one or more nucleic acids encoding a polypeptide (or fragments thereof)) from a second type (e.g., a MorV) or strain (e.g., a VSV strain New Jersey) of vesiculovirus. For example, a chimeric vesiculovirus provided herein can include a first genomic fragment of a VSV and a second genomic fragment of a MorV. A VSV can have a sequence set forth in, for example, National Center for Biotechnology Information (NCBI) Accession Nos: J02428.1 (see, e.g., GI: 335873), KT429217.1 (see, e.g., GI: 983657304), and NC 001560.1 (see, e.g., GI: 9627229). A MorV can have a sequence set forth in, for example, NCBI Accession Nos: NC_034508.1 (see, e.g., GI: 1192699156), and KM205007.1 (see, e.g., GI: 765198376).

In some cases, nucleic acid encoding a polypeptide (or fragments thereof) also can include one or both IGRs (or fragments thereof). For example, when chimeric vesiculoviruses described herein (e.g., a VSV-MorV-G) include nucleic acid encoding a polypeptide (or fragments thereof) from a first vesiculovirus (e.g., a VSV) and nucleic acid encoding a polypeptide (or fragments thereof) from a second different vesiculovirus (e.g., a MorV), the nucleic acid encoding a polypeptide (or fragments thereof) from the second vesiculovirus can include one or both IGRs (or fragments thereof). An IGR can include any appropriate number of nucleotides. For example, an IGR can include from about 25 nucleotides to about 60 nucleotides (e.g., from about 25 nucleotides to about 55 nucleotides, from about 25 nucleotides to about 50 nucleotides, from about 25 nucleotides to about 45 nucleotides, from about 25 nucleotides to about 40 nucleotides, from about 25 nucleotides to about 35 nucleotides, from about 30 nucleotides to about 60 nucleotides, from about 35 nucleotides to about 60 nucleotides, from about 40 nucleotides to about 60 nucleotides, from about 45 nucleotides to about 60 nucleotides, from about 50 nucleotides to about 60 nucleotides, from about 30 nucleotides to about 50 nucleotides, from about 35 nucleotides to about 45 nucleotides, from about 30 nucleotides to about 45 nucleotides, or from about 35 nucleotides to about 50 nucleotides). In some cases, an IGR can include about 24 nucleotides or about 25 nucleotides. In some cases, an IGR can include about 40 nucleotides or about 41 nucleotides. In some cases, nucleic acid encoding a polypeptide (or fragments thereof) can include a 3' IGR. A 3' IGR can be an IGR present between nucleic acid encoding a M polypeptide and nucleic acid encoding a G polypeptide present in a vesiculovirus. An exemplary 3' IGR can include the nucleotide sequence set forth in SEQ ID NO:1 (see, e.g., FIG. 1). In some cases, nucleic acid encoding a polypeptide (or fragments thereof) can include a 5' IGR. A5' IGR can be an IGR present between nucleic acid encoding a G polypeptide and nucleic acid encoding a L polypeptide present in a vesiculovirus. An exemplary 5' IGR can include the nucleotide sequence set forth in SEQ ID NO:2 (see, e.g., FIG. 1). In some cases, nucleic acid encoding a polypeptide (or fragments thereof) can include both a 3' IGR and a 5' IGR.

In some cases, chimeric vesiculoviruses described herein (e.g., a VSV-MorV-G) can include a VSV genome that includes nucleic acid encoding a polypeptide (or fragments thereof) from a MorV. For example, a chimeric vesiculovirus having oncolytic anti-cancer activity can include nucleic acid encoding a N polypeptide, nucleic acid encoding a P polypeptide, nucleic acid encoding a M polypeptide, and nucleic acid encoding a L polypeptide from a VSV; and can include nucleic acid encoding a G polypeptide and its IGRs from a MorV (see, e.g., FIG. 1).

Chimeric vesiculoviruses described herein (e.g., a VSV-MorV-G) that include nucleic acid encoding a N polypeptide, nucleic acid encoding a P polypeptide, nucleic acid encoding a M polypeptide, and nucleic acid encoding a L polypeptide from a VSV, and that include nucleic acid encoding a G polypeptide and its IGRs from a MorV can include any appropriate nucleotide sequence. An exemplary nucleotide sequence of a chimeric vesiculovirus that includes nucleic acid encoding a N polypeptide, nucleic acid encoding a P polypeptide, nucleic acid encoding a M polypeptide, and nucleic acid encoding a L polypeptide from a VSV, and that includes nucleic acid encoding a G polypeptide and its IGRs from a MorV includes, without limitation, the nucleotide sequence set forth in SEQ ID NO:3 (see, e.g., FIG. 2). In some cases, the nucleotide sequence of a chimeric vesiculovirus that includes nucleic acid encoding a N polypeptide, nucleic acid encoding a P polypeptide, nucleic acid encoding a M polypeptide, and nucleic acid encoding a L polypeptide from a VSV, and that includes nucleic acid encoding a G polypeptide and its IGRs from a MorV can have a sequence that deviates from the nucleotide sequence set forth in SEQ ID NO:3, sometimes referred to as a variant sequence. For example, a chimeric vesiculovirus described herein can have a nucleotide sequence that includes one or more modifications to the nucleotide sequence set forth in SEQ ID NO:3. A modification can be any type of modification. Examples of modifications that can be made to a nucleotide sequence include, without limitation, deletions, insertions, and substitutions. In some cases, a modification can be a silent modification (e.g., a modification to nucleic acid encoding a polypeptide that does not produce a modification in the encoded polypeptide). For example, a nucleotide sequence of a chimeric vesiculovirus that includes nucleic acid encoding a N polypeptide, nucleic acid encoding a P polypeptide, nucleic acid encoding a M polypeptide, and nucleic acid encoding a L polypeptide from a VSV, and that includes nucleic acid encoding a G polypeptide and its IGRs from a MorV can have at least 80% sequence identity (e.g., about 82% sequence identity, about 85% sequence identity, about 88% sequence identity, about 90% sequence identity, about 93% sequence identity, about 95% sequence identity, about 97% sequence identity, about 98% sequence identity, or about 99% sequence identity) to the nucleotide sequences set forth in SEQ ID NO:3. Percent sequence identity is calculated by determining the number of matched positions in aligned nucleotide sequences, dividing the number of matched positions by the total number of aligned nucleotide, respectively, and multiplying by 100. A matched position refers to a position in which identical nucleotide occur at the same position in aligned sequences. Sequences can be aligned using the algorithm described by Altschul et al. (Nucleic Acids Res., 25:3389-3402 (1997)) as incorporated into BLAST (basic local alignment search tool) programs, available at ncbi.nlm.nih.gov on the World Wide Web. BLAST searches or alignments can be performed to determine percent sequence identity between a nucleic acid and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a nucleotide sequence and another sequence, the default parameters of the respective programs can be used.

In some cases, chimeric vesiculoviruses described herein (e.g., a VSV-MorV-G) can include nucleic acid encoding a polypeptide (e.g., a transgene). A nucleic acid encoding a polypeptide can encode any appropriate polypeptide. In some cases, a polypeptide can be a detectable label. Examples of detectable labels include, without limitation, fluorophores (e.g., green fluorescent protein (GFP), mCherry, and yellow fluorescent protein (YFP)), enzymes (e.g., luciferase), and surface transport proteins (e.g. sodium iodide symporter). Examples of other polypeptides that can be encoded by a transgene in a chimeric vesiculovirus provided herein include, without limitation, targeting polypeptides (e.g., A20 peptide, and single chain variable fragments (scFvs)), transport polypeptides (e.g., nuclear localization sequences (NLSs)), transporter polypeptides (e.g., sodium iodine symporter polypeptides, and somatostatin Receptor 2), therapeutic polypeptides (e.g., TP53, and CDKN2A (p16)), and cytotoxic polypeptides (e.g., thymidine kinases, and caspases).

This document also provides methods and materials for using one or more chimeric vesiculoviruses provided herein (e.g., a VSV-MorV-G). In some cases, one or more chimeric vesiculoviruses provided herein can used for treating a mammal in need thereof (e.g., a human having cancer). For example, one or more chimeric vesiculoviruses provided herein (e.g., a composition including one or more chimeric vesiculoviruses provided herein) can be administered to a mammal having cancer to treat the mammal. In some cases, administering one or more chimeric vesiculoviruses provided herein to a mammal (e.g., a human) having cancer can increase survival of the mammal. In some cases, administering one or more chimeric vesiculoviruses provided herein to a mammal (e.g., a human) having cancer can stimulate an anti-cancer immune response in the mammal.

In some cases, one or more chimeric vesiculoviruses provided herein (e.g., a VSV-MorV-G) can be administered to a mammal to reduce the size of the cancer in the mammal (e.g., reduce the number of cancer cells in the mammal and/or the volume of one or more tumors in the mammal). For example, one or more chimeric vesiculoviruses provided herein can be administered to a mammal (e.g., a human) in need thereof (e.g., a human having cancer) as described herein to reduce the size of the cancer by, for example, 10, 20, 30, 40, 50, 60, 70, 80, 90, 95, or more percent.

In some cases, one or more chimeric vesiculoviruses provided herein (e.g., a VSV-MorV-G) can be administered to a mammal to induce oncolysis of cancer cells within a mammal. For example, one or more chimeric vesiculoviruses provided herein can be administered to a mammal to induce cell death in a cell of the mammal (e.g., in an infected cell of the mammal). For example, one or more chimeric vesiculoviruses provided herein can be administered to a mammal (e.g., a human) in need thereof (e.g., a human having cancer) as described herein to induce oncolysis in, for example, 10, 20, 30, 40, 50, 60, 70, 80, 90, 95, or more percent of the cancer cells in the mammal.

In some cases, one or more chimeric vesiculoviruses provided herein (e.g., a VSV-MorV-G) can be administered to a mammal to induce a cytopathogenic effect (CPE) in a cell of the mammal. For example, one or more chimeric vesiculoviruses provided herein can be administered to a mammal to induce syncytia formation of a cell of the mammal (e.g., of an infected cell of the mammal). For example, one or more chimeric vesiculoviruses provided herein can be administered to a mammal to induce vacuolization of a cell of the mammal (e.g., of an infected cell of the mammal). For example, one or more chimeric vesiculoviruses provided herein can be administered to a mammal (e.g., a human) in need thereof (e.g., a human having cancer) as described herein to induce a CPE in, for example, 10, 20, 30, 40, 50, 60, 70, 80, 90, 95, or more percent of the cancer cells in the mammal.

Any appropriate mammal having, or at risk of having, cancer can be treated as described herein. Examples of mammal that can have, or can be at risk of having, cancer and can be treated as described herein (e.g., by administering one or more chimeric vesiculoviruses provided herein such as VSV-MorV-G) include, without limitation, humans, non-human primates such as monkeys, horses, bovine species, porcine species, dogs, cats, mice, and rats. In some cases, a human having cancer can be treated. In some cases, a mammal (e.g., a human) treated as described herein is not a natural host of (e.g., does not have immunity against) a vesiculovirus used to generate a chimeric vesiculoviruses provided herein (e.g., a VSV-MorV-G). For example, a human being treated with a chimeric vesiculoviruses provided herein (e.g., a VSV-MorV-G) can lack any pre-existing adaptive immunity to VSV and/or MorV.

A mammal having any type of cancer can be treated as described herein (e.g., by administering one or more chimeric vesiculoviruses provided herein). In some cases, a cancer treated as described herein can include one or more solid tumors. In some cases, a cancer treated as described herein can be a hematologic cancer (e.g., a blood cancer). Examples of cancers that can be treated as described herein include, without limitation, hepatobiliary cancers, pancreatic cancers, glioblastoma, leukemia, lymphoma, and myeloma.

In some cases, methods described herein also can include identifying a mammal as having cancer. Examples of methods for identifying a mammal as having cancer include, without limitation, physical examination, laboratory tests (e.g., blood and/or urine tests), biopsy, imaging tests (e.g., X-ray, PET/CT, MRI, and/or ultrasound), nuclear medicine scans (e.g., bone scans), endoscopy, genetic tests, and/or histopathological evaluation. Once identified as having cancer, a mammal can be administered or instructed to self-administer one or more chimeric vesiculoviruses provided herein (e.g., one or more chimeric vesiculoviruses having oncolytic anti-cancer activity) or a nucleic acid (e.g., an expression vector) encoding one or more chimeric vesiculoviruses provided herein.

One or more chimeric vesiculoviruses provided herein (e.g., a VSV-MorV-G) can be administered by any appropriate route, e.g., intravenous, intramuscular, subcutaneous, oral, intranasal, inhalation, transdermal, and parenteral, to a mammal. In some cases, one or more recombinant vesiculoviruses described herein can be administered intravenously to a mammal (e.g., a human).

In some cases, one or more chimeric vesiculoviruses provided herein (e.g., a VSV-MorV-G) can be formulated into a composition (e.g., a pharmaceutical composition) for administration to a mammal (e.g., a mammal having, or at risk of having, cancer). For example, one or more chimeric vesiculoviruses provided herein can be formulated into a pharmaceutically acceptable composition for administration to a mammal having, or at risk of having, cancer. In some cases, one or more chimeric vesiculoviruses provided herein can be formulated together with one or more pharmaceutically acceptable carriers (additives), excipients, and/or diluents. Examples of pharmaceutically acceptable carriers, excipients, and diluents that can be used in a composition described herein include, without limitation, sucrose, lactose, starch (e.g., starch glycolate), cellulose, cellulose derivatives (e.g., modified celluloses such as microcrystalline cellulose and cellulose ethers like hydroxypropyl cellulose (HPC) and cellulose ether hydroxypropyl methylcellulose (HPMC)), xylitol, sorbitol, mannitol, gelatin, polymers (e.g., polyvinylpyrrolidone (PVP), polyethylene glycol (PEG), crosslinked polyvinylpyrrolidone (crospovidone), carboxymethyl cellulose, polyethylene-polyoxypropylene-block polymers, and crosslinked sodium carboxymethyl cellulose (croscarmellose sodium)), titanium oxide, azo dyes, silica gel, fumed silica, talc, magnesium carbonate, vegetable stearin, magnesium stearate, aluminum stearate, stearic acid, antioxidants (e.g., vitamin A, vitamin E, vitamin C, retinyl palmitate, and selenium), citric acid, sodium citrate, parabens (e.g., methyl paraben and propyl paraben), petrolatum, dimethyl sulfoxide, mineral oil, serum proteins (e.g., human serum albumin), glycine, sorbic acid, potassium sorbate, water, salts or electrolytes (e.g., saline, protamine sulfate, disodium hydrogen phosphate, potassium hydrogen phosphate, sodium chloride, and zinc salts), colloidal silica, magnesium trisilicate, polyacrylates, waxes, wool fat, and lecithin.

A composition (e.g., a pharmaceutical composition) containing one or more chimeric vesiculoviruses provided herein (e.g., a VSV-MorV-G) can be formulated into any appropriate dosage form. Examples of dosage forms include solid or liquid forms including, without limitation, liquids, enemas, suspensions, solutions (e.g., sterile solutions), sustained-release formulations, delayed-release formulations, pills, powders, and granules.

A composition (e.g., a pharmaceutical composition) containing one or more chimeric vesiculoviruses provided herein (e.g., a VSV-MorV-G) can be designed for parenteral (including subcutaneous, intratumoral, intramuscular, intravenous, topical, and intradermal) administration. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders.

A composition (e.g., a pharmaceutical composition) containing one or more chimeric vesiculoviruses provided herein (e.g., a VSV-MorV-G) can be administered locally or systemically. For example, a composition containing one or more chimeric vesiculoviruses provided herein can be administered locally by an intratumoral injection to a tumor within a mammal (e.g., a human). For example, a composition containing one or more chimeric vesiculoviruses provided herein can be administered systemically by intravenous administration to a mammal (e.g., a human).

An effective amount (e.g., effective dose) of one or more chimeric vesiculoviruses provided herein (e.g., a VSV-MorV-G) can vary depending on the severity of the cancer, the route of administration, the age and general health condition of the subject, excipient usage, the possibility of co-usage with other therapeutic treatments such as use of other agents, and/or the judgment of the treating physician.

An effective amount of a composition (e.g., a pharmaceutical composition) containing one or more chimeric vesiculoviruses provided herein (e.g., a VSV-MorV-G) can be any amount that can treat the cancer without producing significant toxicity to the mammal. An effective amount of one or more chimeric vesiculoviruses provided herein can be any appropriate amount. In some cases, an effective amount of a chimeric vesiculovirus such as VSV-MorV-G can be from about $1\times10^2$ $TCID_{50}$ (tissue culture infective dose) per dose to about $1\times10^7$ $TCID_{50}$ per dose (e.g., from about $1\times10^2$ $TCID_{50}$ per dose to about $1\times10^6$ $TCID_{50}$ per dose, from about $1\times10^2$ $TCID_{50}$ per dose to about $1\times10^5$ $TCID_{50}$ per dose, from about $1\times10^2$ $TCID_{50}$ per dose to about $1\times10^4$ $TCID_{50}$ per dose, from about $1\times10^2$ $TCID_{50}$ per dose to about $1\times10^3$ $TCID_{50}$ per dose, from about $1\times10^3$ $TCID_{50}$ per dose to about $1\times10^7$ $TCID_{50}$ per dose, from about $1\times10^4$ $TCID_{50}$ per dose to about $1\times10^7$ $TCID_{50}$ per dose, from about $1\times10^5$ $TCID_{50}$ per dose to about $1\times10^7$ $TCID_{50}$ per dose, from about $1\times10^6$ $TCID_{50}$ per dose to about $1\times10^7$ $TCID_{50}$ per dose, from about $1\times10^3$ $TCID_{50}$ per dose to about $1\times10^6$ $TCID_{50}$ per dose, or from about $1\times10^4$ $TCID_{50}$ per dose to about $1\times10^5$ $TCID_{50}$ per dose). In some cases, an effective amount of a chimeric vesiculovirus such as VSV-MorV-G can be from about $1\times10^6$ $TCID_{50}$ per kilogram body weight ($TCID_{50}$/kg) to about $1\times10^9$ $TCID_{50}$/kg (e.g., from about $1\times10^6$ $TCID_{50}$/kg to about $1\times10^8$ $TCID_{50}$/kg, from about $1\times10^6$ $TCID_{50}$/kg to about $1\times10^7$ $TCID_{50}$/kg, from about $1\times10^7$ $TCID_{50}$/kg to about $1\times10^9$ $TCID_{50}$/kg, from about $1\times10^8$ $TCID_{50}$/kg to about $1\times10^9$ $TCID_{50}$/kg, or from about $1\times10^7$ $TCID_{50}$/kg to about $1\times10^8$ $TCID_{50}$/kg). The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., a cancer) may require an increase or decrease in the actual effective amount administered.

The frequency of administration of a composition (e.g., a pharmaceutical composition) containing one or more chimeric vesiculoviruses provided herein (e.g., a VSV-MorV-G) can be any frequency that can treat the cancer without producing significant toxicity to the mammal. For example, the frequency of administration can be from about three times a day to about once a week, from about twice a day to about twice a week, or from about once a day to about twice a week. The frequency of administration can remain constant or can be variable during the duration of treatment. A course of treatment with a composition containing one or more chimeric vesiculoviruses provided herein can include rest periods. For example, a composition containing one or more chimeric vesiculoviruses provided herein can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., a cancer) may require an increase or decrease in administration frequency.

An effective duration for administering a composition (e.g., a pharmaceutical composition) containing one or more chimeric vesiculoviruses provided herein (e.g., a VSV-MorV-G) can be any duration that treat the cancer without producing significant toxicity to the mammal. For example, the effective duration can vary from several days to several weeks, months, or years. In some cases, the effective duration for the treatment of a cancer can range in duration from about one month to about 10 years. Multiple factors can influence the actual effective duration used for a particular treatment. For example, an effective duration can vary with the frequency of administration, effective amount, use of multiple treatment agents, route of administration, and severity of the condition being treated.

In some cases, methods described herein also can include administering to a mammal (e.g., a mammal having cancer) one or more additional agents used to treat a cancer. The one or more additional agents used to treat a cancer can include any appropriate cancer treatment. In some cases, a cancer treatment can include surgery. In some cases, a cancer treatment can include radiation therapy. In some cases, a cancer treatment can include administration of a pharmacotherapy such as a chemotherapy, hormone therapy, targeted therapy, and/or cytotoxic therapy. For example, a mammal having cancer can be administered one or more chimeric vesiculoviruses provided herein (e.g., a VSV-MorV-G) and administered one or more additional agents used to treat a cancer. In cases where a mammal having cancer is treated with one or more chimeric vesiculoviruses provided herein and is treated with one or more additional agents used to treat a cancer, the additional agents used to treat a cancer can be administered at the same time or independently. For example, one or more chimeric vesiculoviruses provided herein and one or more additional agents used to treat a cancer can be formulated together to form a single composition. In some cases, one or more chimeric vesiculoviruses provided herein can be administered first, and the one or more additional agents used to treat a cancer administered second, or vice versa.

In some cases, the size of the cancer (e.g., the number of cancer cells and/or the volume of one or more tumors) present within a mammal and/or the severity of one or more symptoms of the cancer being treated can be monitored. Any appropriate method can be used to determine whether or not the size of the cancer present within a mammal is reduced. For example, imaging techniques can be used to assess the size of the cancer present within a mammal.

The invention will be further described in the following examples, which do not limit the scope of the invention described in the claims.

EXAMPLES

Example 1: Recombinant VSV to Treat Cancer

Materials and Methods

Wild type morreton virus (MorV) was used to infect BHK-21 cells (ATCC, USA). Full length MorV genome was confirmed by RNA-sequencing. The complete genome of MorV is typical of that of VSV, which includes from 3' end to 5' end five major genes: MorV N polypeptide, MorV P polypeptide, MorV M polypeptide, MorV G polypeptide and MorV L polypeptide. DNA sequence encoding for full-length MorV G polypeptide and the intergenic regions (IGRs) between MorV M and G genes (25 nts) and between MorV G and L genes (41 nts) were synthetized by Genscript, USA.

Using laboratory based cloning methods, the VSV-G gene was removed from plasmid pVSV-XN2 encoding for full-length antisense VSV genome and replaced with the MorV (MorV-G) G gene and its IGRs to produce pVSV-MorV-G.

To rescue infectious VSV-MorV-G particles, BHK-21 cells were infected with vaccinia virus (Kerafast, USA) expressing the T7 RNA polymerase. Vaccinia infected BHK-21 cells were transfected with plasmids encoding for full-length pVSV-MorV-G and pVSV-L, pVSV-N and pVSV-P genes as described elsewhere (Lawson et al., *Proc Natl Acad Sci USA* 92:4477-4481 (1995)). Cell supernatant containing infectious VSV-MorV-G was collected and filtered through 0.22 μm filter (Millipore, USA) to remove the residual vaccinia virus. VSV-MorV-G filtered supernatant was used to infect fresh BHK-21 cells until cytopathic effect (CPE) was readily apparent under light microscope. Complete genome sequence of VSV-MorV-G containing VSV N, M, P and L genes along with MorV G gene and IGRs were confirmed by ISU VDL using deep RNA-sequencing technology.

Results

VSV-MorV-G not only incorporated the fast lytic cycle of VSV, but the potent cancer cell-specific cytotoxic effects of MorV in hepatocellular carcinoma (HCC) and pancreatic cancer (PC) cell models. Moreover, VSV-MorV-G and parental MorV are relatively resistant to anti-VSV neutralizing antibodies.

Design of Chimeric VSV-MorV-G

The VSV-G gene was removed from plasmid pVSV-XN2 encoding for full-length VSV genome and replaced the MorV G gene (MorV-G, 1542 nucleotides) and its 3' and 5' IGRs (66 nucleotides). Recombinant VSVs were rescued by co-transfecting modified pVSV-XN2 plasmids and plasmid coding for VSV-L, VSV-N and VSV-P genes. Schematic Genomes of VSV, MorV, and VSV-MorV-G are shown in FIG. 1 and the nucleotide sequence of the VSV-MorV-G genome (11188 nucleotides) from 3' end to 5'end (antisense genome) containing VSV N, VSV M, VSV P, MorV G and IGRs, and VSV L (SEQ ID NO:3) is shown in FIG. 2.

A plasmid encoding for VSV Mor V N and G genome was engineered, where the N and G genes of VSV were replaced with those of MorV without the IGRs. This plasmid lacking the IGRs failed to produce infectious particles.

Substitution of other VSV genes (N, P, M and L) inhibited the assembly and budding of infectious particles.

Plasmids encoding for VSV-CDV (VSV-G substituted with canine distemper virus envelop proteins) and VSV-SeV FH (VSV-G substituted with sendai virus envelop proteins) failed to produced infectious particles.

Figure 3:
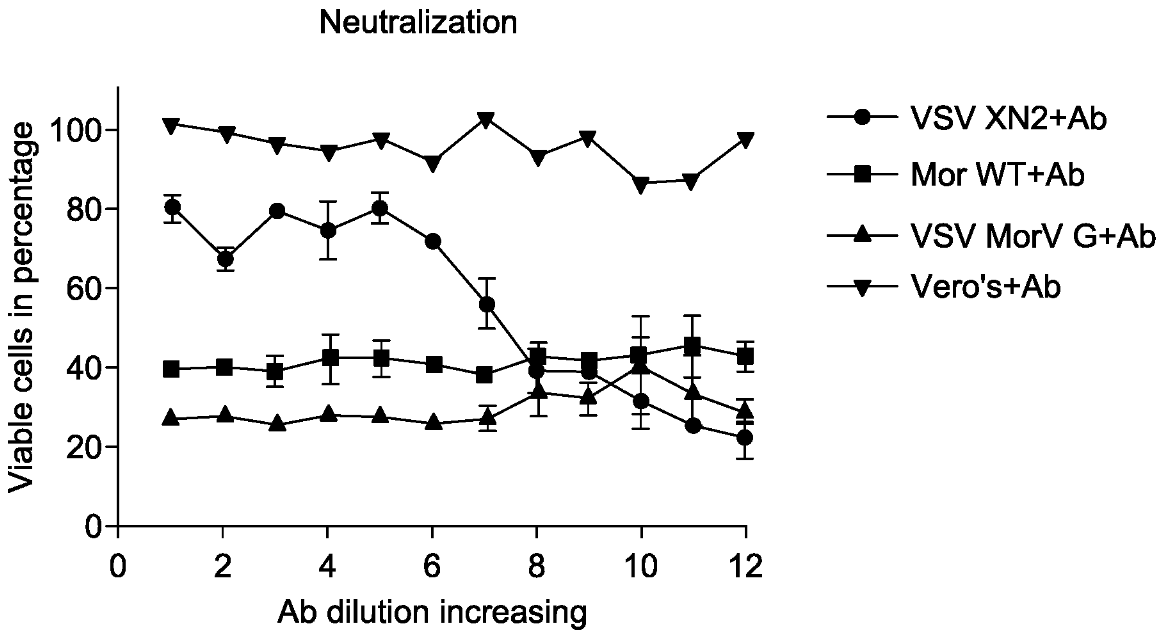
FIG. 3. A graph showing neutralization of wild type VSV (VSVwt; VSV-XN2), wild type MorV (MorVwt), and VSV-MorV-G by VSV neutralizing antibodies.

MorV and VSV-MorV-G are Resistant to Ant-VSV G Antibody 400 (or about $10^4$ copies) $TCID_{50}$/mL (the infectious titer of any virus that can cause 50% of cytopathic effect in tissue culture) of VSVwt (VSV-XN2), MorVwt, and VSV-MorV-G were treated with a 2-fold twelve point dilution of neutralizing VSV antibodies (Kerafast, USA) and incubated for 1 hour at 37 degree Celsius in a 5% CO2 incubator. Followed by addition of 20,000 Vero cells (ATCC, USA) and 24 hours incubation. Cell viability analysis using MTS Cell proliferation assay (Promega, USA) showed that MorVwt and VSV-MorV-G induced significantly higher cytotoxicity compared to VSV-XN2, thus are relatively more resistant to VSV neutralizing antibodies (FIG. 3).

Figure 4A:
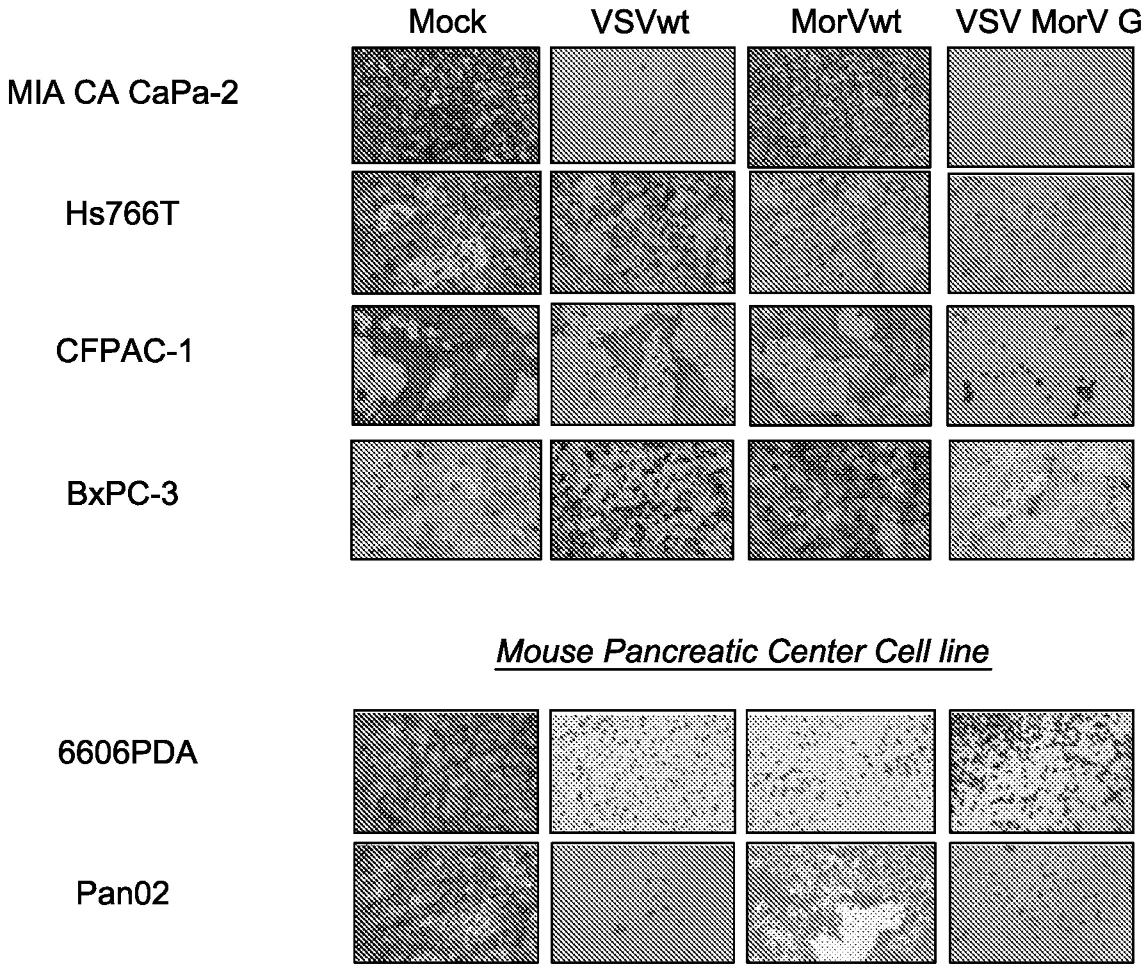
FIGS. 4A and 4B. Oncolysis in human and mouse pancreatic cancer cell lines following infection with wild type VSV (VSVwt), wild type MorV (MorVwt), or the hybrid VSV-MorV-G.

VSV-MorV-G to Treat Pancreatic Cancer 200,000 human or mouse pancreatic cancer cell lines were either mock infected or infected with VSVwt, MorVwt, or VSV-MorV-G at a multiplicity of infection (MOI) of 0.01 for 30 minutes. Cells were washed with un-supplemented media and incubated with complete media for 48 hours. After incubation media was removed in each well and cells were stained for 10 minutes with 0.1% crystal violet in 20% glutaraldehyde. Pictures (10×) were taken with Evos Cells Imaging System microscope (Thermofischer, USA). VSV-MorV-G induced oncolysis in pancreatic cancer cells (FIG. 4A).

Figure 4B:
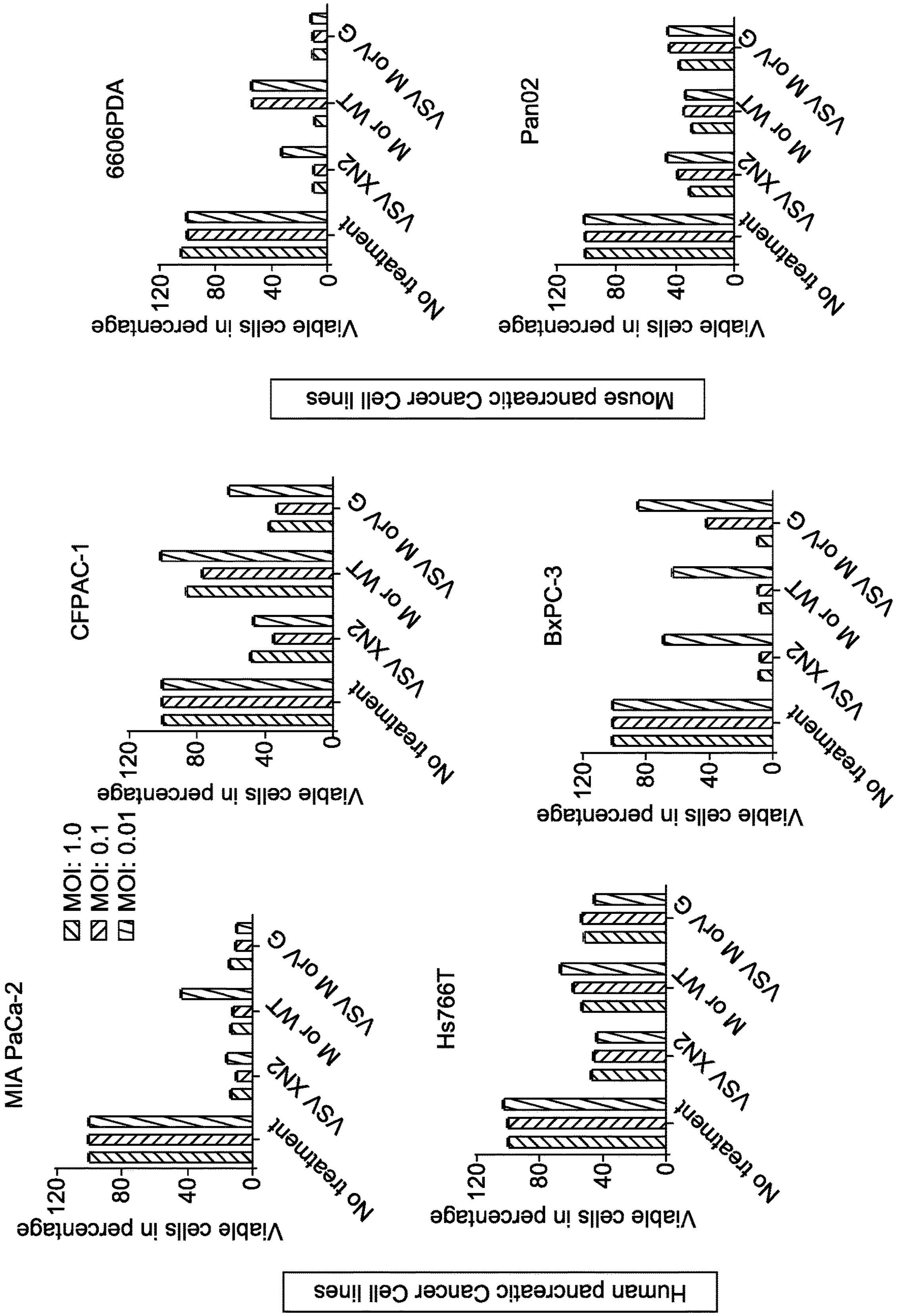

15,000 human or mouse pancreatic cancer cell lines were either mock infected or infected with VSVwt, MorVwt, or VSV-MorV-G at MOI of 1.0, 0.1, or 0.01 for 72 hours. Cell viability was assessed using MTT assay following manufacturer's instructions (Promega, USA). VSV-MorV-G induced CPE in pancreatic cancer cells (FIG. 4B).

Figure 5A:
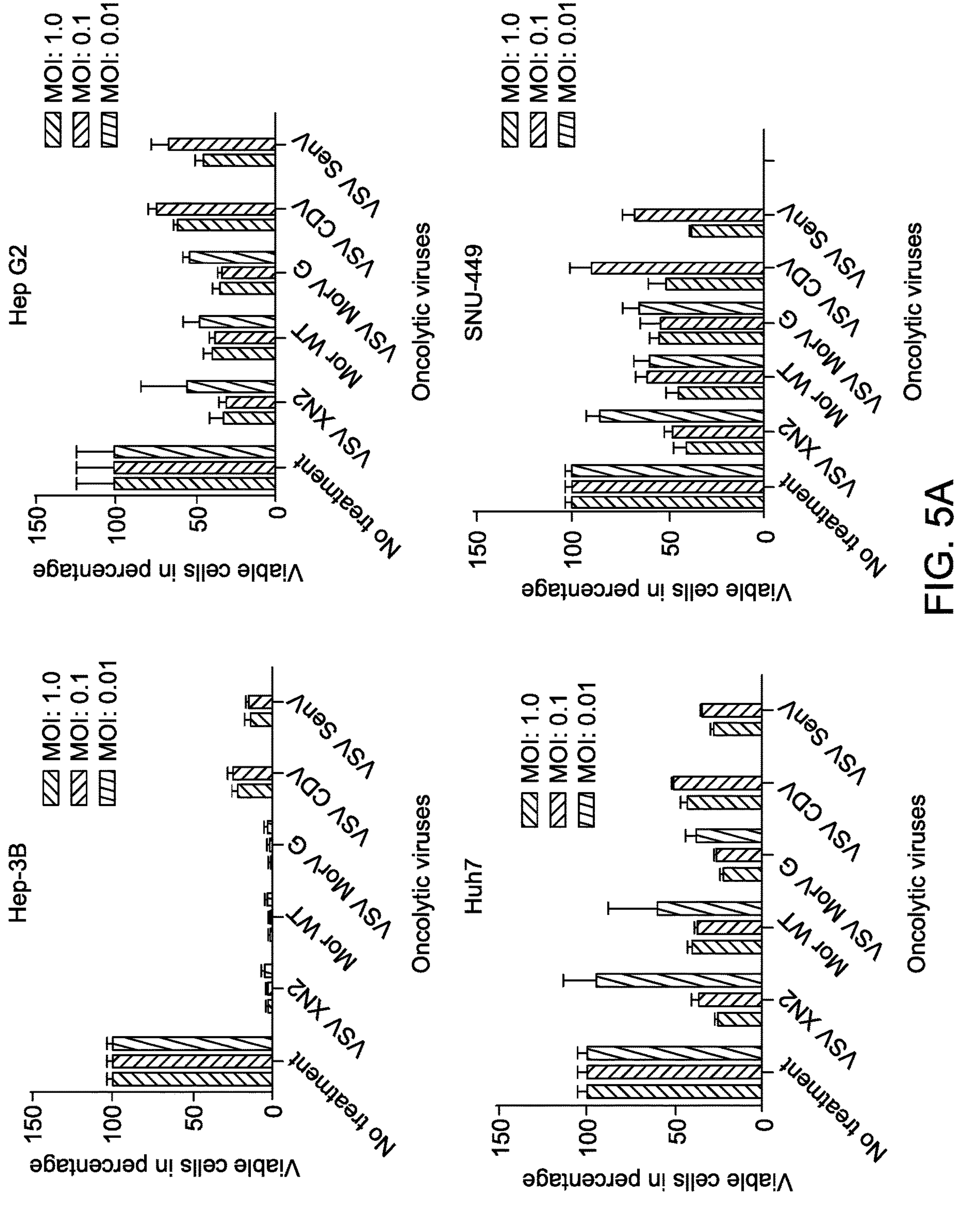
FIGS. 5A and 5B. Cytopathogenic effect (CPE) in human hepatocellular carcinoma (HCC) cell lines following infection with wild type VSV (VSVwt), wild type MorV (MorVwt), or the hybrid VSV-MorV-G.
Figure 5B:
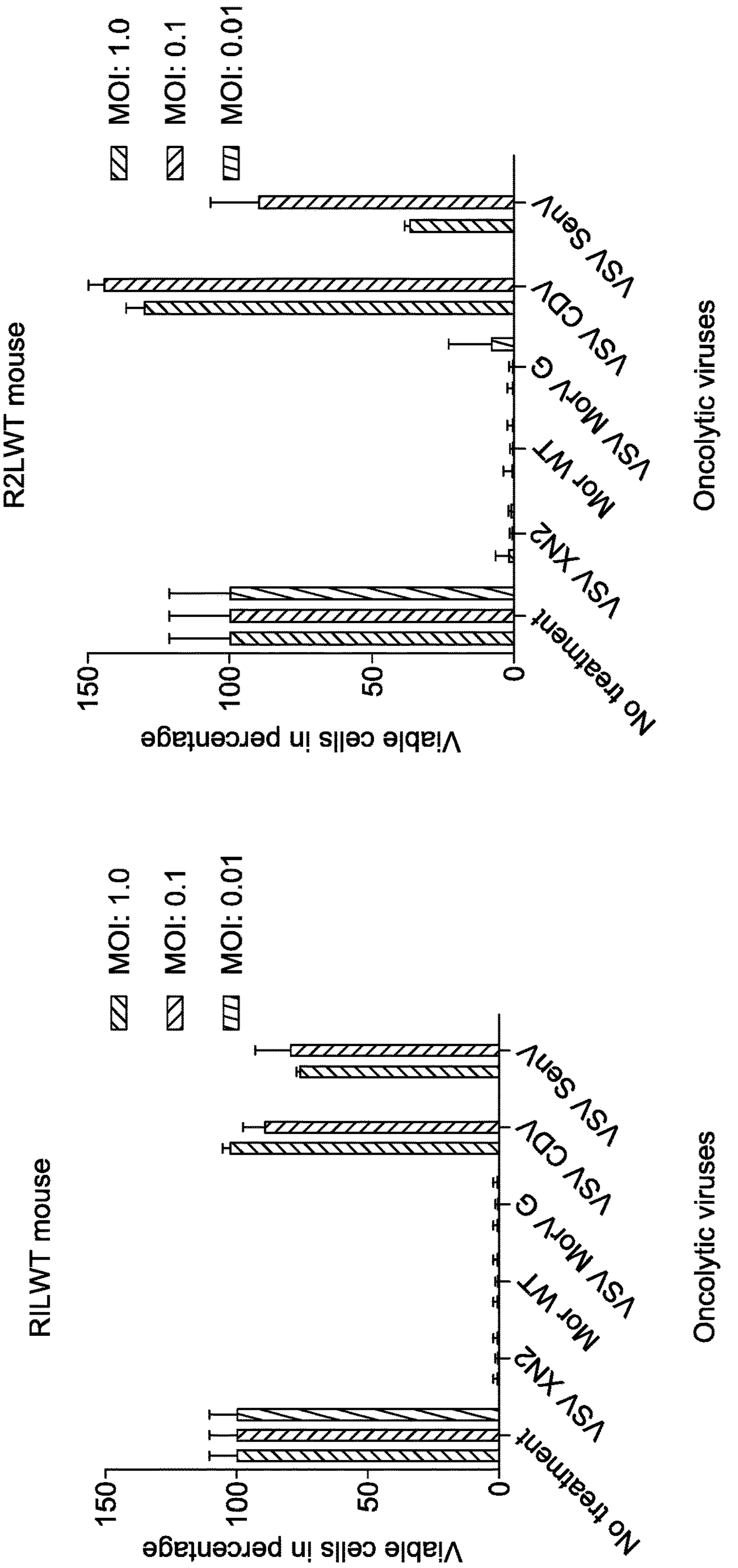

VSV-MorV-G to Treat HCC 15,000 human hepatocellular carcinoma (HCC) cell lines and mouse HCC cell lines were either mock infected or infected with VSVwt, MorVwt, or VSV-MorV-G at MOI of 1.0, 0.1, or 0.01 for 72 hours. Cell viability was assessed using MTT assay following manufacturer's instructions (Promega, USA). VSV-MorV-G induced CPE in HCC cells (FIGS. 5A and 5B).

Example 2: Potency of Recombinant VSV in Liver Cancer

A syngeneic mouse model for liver cancer was established by injecting bile duct cancer cells directly into the livers of mice.

Mice having established liver tumors were intraperitoneally injected with a single dose of either oncolytic MorV (at $10^7$ tissue culture dose 50 ($TCID_{50}$) or at $10^8$ $TCID_{50}$ per mouse) or VSV (at $10^7$ $TCID_{50}$ or $10^8$ $TCID_{50}$ per mouse). Control animals were intraperitoneally injected with phosphate-buffered saline (PBS).

Figure 6:
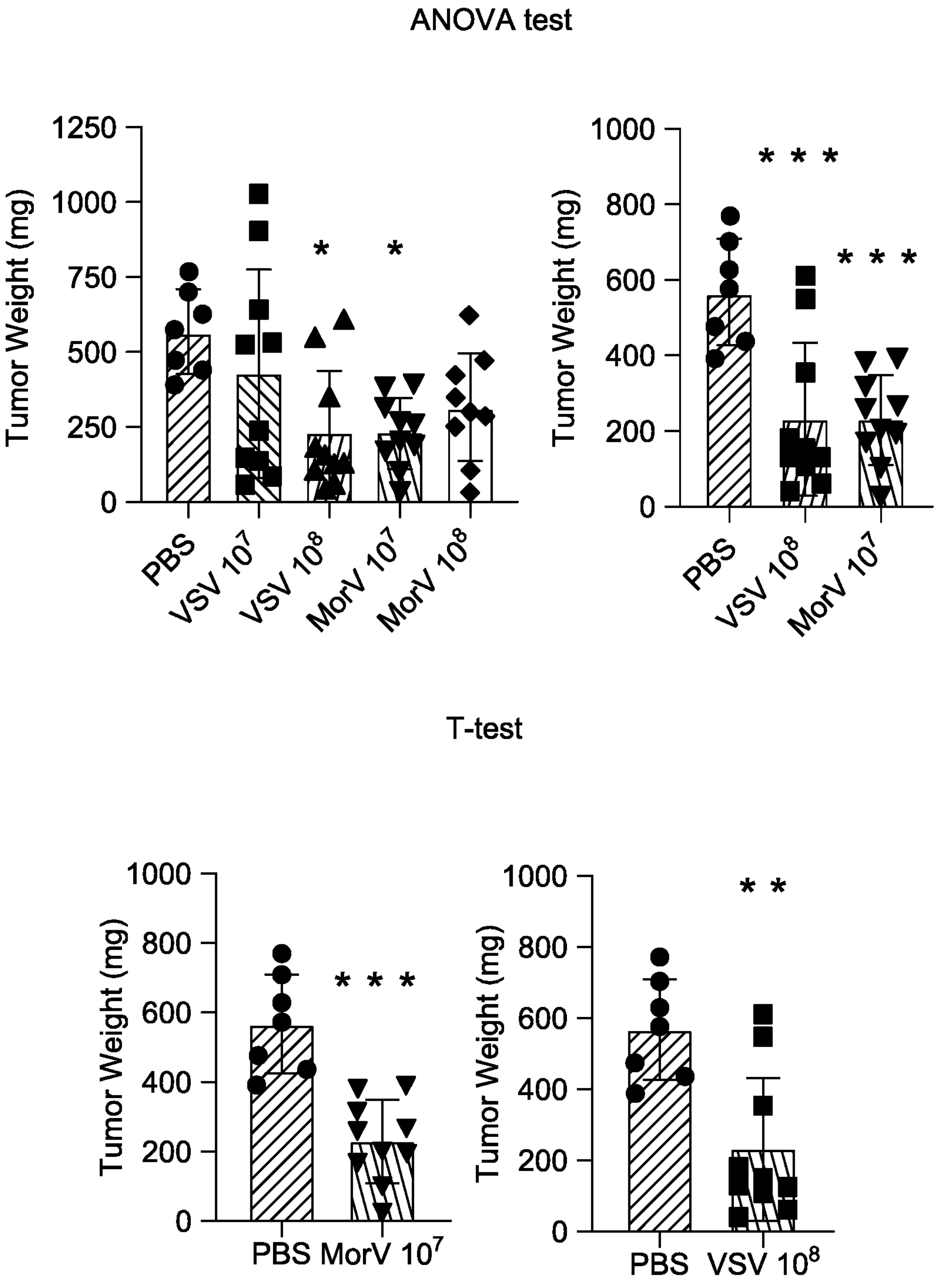
FIG. 6. Tumor weight of liver tumors in syngeneic mice following intraperitoneal administration of a single dose of either phosphate-buffered saline (PBS), oncolytic morreton virus (MorV), or vesicular stomatitis virus (VSV).

Approximately, three weeks after treatment, mice were sacrificed and remaining tumors were surgically removed from the liver and weighed. Animals treated with MorV exhibited a significantly higher oncolytic activity compared to animals treated with VSV. Mice treated with MorV at TCID50 $10^7$ showed noticeable tumor regressions, and similar oncolytic activity was seen with VSV at $10^8$ TCID50 per mouse (FIG. 6).

Figure 7:
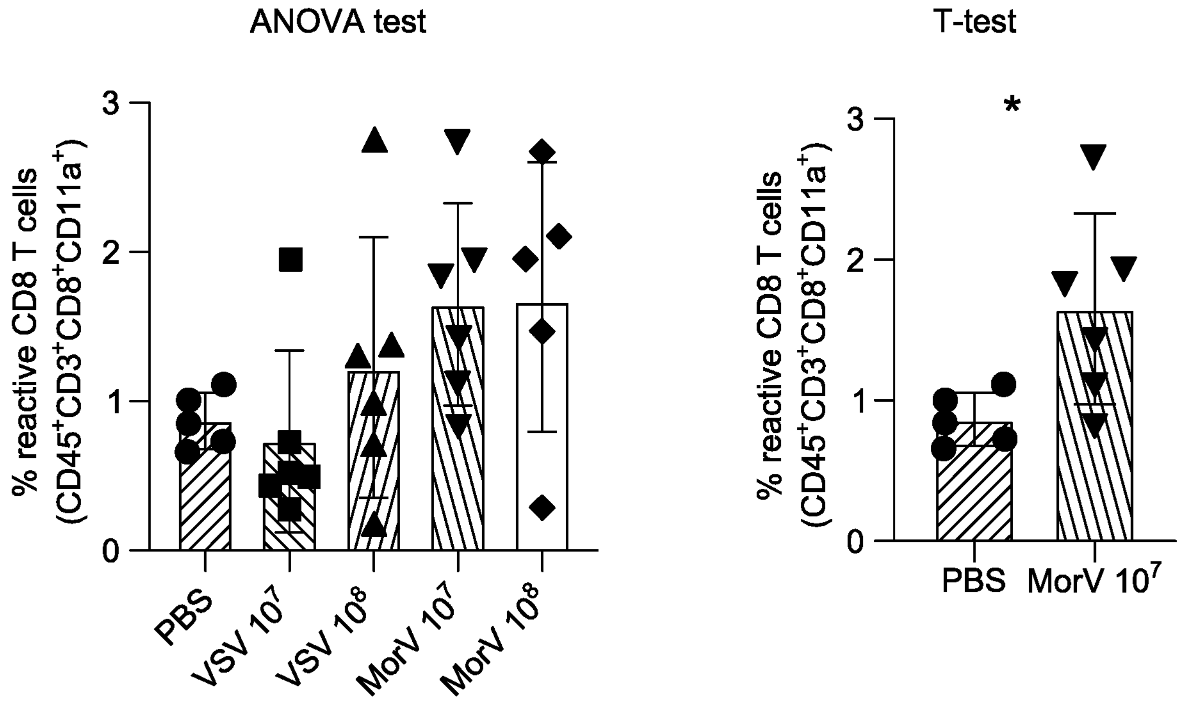
FIG. 7. Reactive CD8+ T cells in untreated (PBS) tumor samples and in tumor samples treated with either MorV or VSV.
Figure 8:
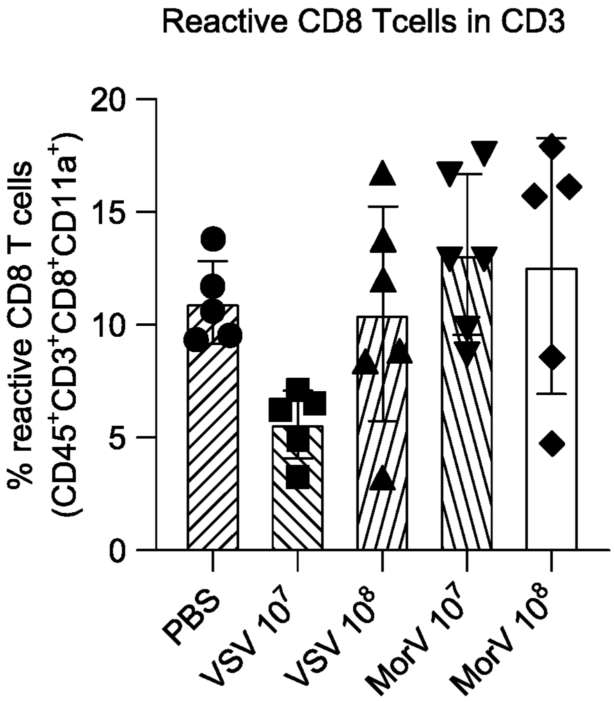
FIG. 8. Proportion of reactive CD8+ T cells in all tumor infiltrating lymphocytes in untreated (PBS) tumor samples and in tumor samples treated with either MorV or VSV.

To examine the immune response induced by VSV-MorV-G within the syngeneic mouse model for liver cancer, flow cytometry analysis was done on treated (MorV, VSV) and untreated (PBS) tumor samples. MorV elicited a robust $CD8^+$ T cells response at 10-fold lower dose ($10^7$ TCID50) compared to VSV (FIG. 7).

Together these results demonstrate that VSV-MorV-G can elicit a robust immune response against liver cancer cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A chimeric vesiculovirus comprising:

(a) a first genomic fragment of a first vesiculovirus species, wherein said first vesiculovirus species is a vesicular stomatitis virus (VSV); and (b) a second genomic fragment of a second vesiculovirus species different from said first vesiculovirus species, wherein said second vesiculovirus species is a Morreton virus (MORV).

2. The chimeric vesiculovirus of claim 1, wherein said first genomic fragment of said first vesiculovirus species comprises nucleic acid encoding a N polypeptide, nucleic acid encoding a P polypeptide, nucleic acid encoding a M polypeptide, and nucleic acid encoding a L polypeptide, and wherein said second genomic fragment of said second vesiculovirus species comprises nucleic acid encoding a G polypeptide and comprises a 3' intergenic region (IGR) and a 5' IGR.

3. The chimeric vesiculovirus of claim 2, wherein said 3' IGR comprises 24 nucleotides or 25 nucleotides.

4. The chimeric vesiculovirus of claim 3, wherein said 3' IGR comprises a nucleotide sequence set forth in SEQ ID NO:1.

5. The chimeric vesiculovirus of claim 2, wherein said 5' IGR comprises 40 nucleotides or 41 nucleotides.

6. The chimeric vesiculovirus of claim 5, wherein said 5' IGR comprises a nucleotide sequence set forth in SEQ ID NO:2.

7. The chimeric vesiculovirus of claim 1, wherein said chimeric vesiculovirus comprises a nucleotide sequence having at least 80% sequence identity to the nucleotide sequence set forth in SEQ ID NO:3.

8. The chimeric vesiculovirus of claim 1, wherein said chimeric vesiculovirus comprises a nucleotide sequence set forth in SEQ ID NO:3.

9. A method for treating a mammal having cancer, wherein said method comprises administering, to said mammal, a chimeric vesiculovirus having oncolytic anti-cancer activity, wherein said chimeric vesiculovirus comprises (a) a first genomic fragment of a first vesiculovirus species, wherein said first vesiculovirus species is a vesicular stomatitis virus (VSV) and (b) a second genomic fragment of a second vesiculovirus species different from said first vesiculovirus species, wherein said second vesiculovirus species is a Morreton virus (MORV).

10. The method of claim 9, wherein said mammal is a human.

11. The method of claim 9, wherein said cancer is selected from the group consisting of hepatobiliary cancer, pancreatic cancer, glioblastoma, leukemia, lymphoma, and myeloma.

12. The method of claim 9, wherein said first genomic fragment of said first vesiculovirus species comprises nucleic acid encoding a N polypeptide, nucleic acid encoding a P polypeptide, nucleic acid encoding a M polypeptide, and nucleic acid encoding a L polypeptide, and wherein said second genomic fragment of said second vesiculovirus species comprises nucleic acid encoding a G polypeptide and comprises a 3' intergenic region (IGR) and a 5' IGR.

13. The method of claim 12, wherein said 3' IGR comprises 24 nucleotides or 25 nucleotides.

14. The method of claim 13, wherein said 3' IGR comprises a nucleotide sequence set forth in SEQ ID NO:1.

15. The method of claim 12, wherein said 5' IGR comprises 40 nucleotides or 41 nucleotides.

16. The method of claim 15, wherein said 5' IGR comprises a nucleotide sequence set forth in SEQ ID NO:2.

17. The method of claim 9, wherein said chimeric vesiculovirus comprises a nucleotide sequence having at least 80% sequence identity to the nucleotide sequence set forth in SEQ ID NO:3.

18. The method of claim 9, wherein said chimeric vesiculovirus comprises a nucleotide sequence set forth in SEQ ID NO:3.

* * * * *